(12) United States Patent
Kasai

(10) Patent No.: US 11,484,187 B2
(45) Date of Patent: Nov. 1, 2022

(54) ENDOSCOPE OBJECTIVE OPTICAL SYSTEM

(71) Applicant: OLYMPUS CORPORATION, Hachioji (JP)

(72) Inventor: Ken Kasai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 842 days.

(21) Appl. No.: 16/410,034

(22) Filed: May 13, 2019

(65) Prior Publication Data

US 2019/0261833 A1 Aug. 29, 2019

Related U.S. Application Data

(63) Continuation of application No. PCT/JP2017/047131, filed on Dec. 27, 2017.

(30) Foreign Application Priority Data

Dec. 28, 2016 (JP) ................. 2016-255818

(51) Int. Cl.
*A61B 1/00* (2006.01)
*A61B 1/045* (2006.01)
*A61B 1/06* (2006.01)
*G02B 13/04* (2006.01)

(52) U.S. Cl.
CPC ...... *A61B 1/00096* (2013.01); *A61B 1/00188* (2013.01); *A61B 1/045* (2013.01); *A61B 1/0676* (2013.01); *G02B 13/04* (2013.01)

(58) Field of Classification Search
CPC . A61B 1/00096; A61B 1/00188; A61B 1/045; A61B 1/0676; G02B 13/04

USPC .................................................... 359/656
See application file for complete search history.

(56) References Cited

U.S. PATENT DOCUMENTS

| | | | |
|---|---|---|---|
| 2010/0020408 A1* | 1/2010 | Noguchi | G02B 23/2438 359/676 |
| 2011/0235192 A1 | 9/2011 | Uzawa et al. | |
| 2016/0238819 A1* | 8/2016 | Sun | G02B 13/02 |
| 2016/0274335 A1 | 9/2016 | Kawamura | |

(Continued)

FOREIGN PATENT DOCUMENTS

| | | |
|---|---|---|
| CN | 105988204 A | 10/2016 |
| JP | 4834799 B2 | 12/2011 |

(Continued)

OTHER PUBLICATIONS

Chinese Office Action (and English language translation thereof) dated Jul. 26, 2021, issued in counterpart Chinese Application No. 201780071769.4.

(Continued)

*Primary Examiner* — Allen C Wong
(74) *Attorney, Agent, or Firm* — Holtz, Holtz & Volek PC

(57) ABSTRACT

The endoscope objective optical system includes in order from an object side, a first lens group having a positive refractive power, a second lens group having a negative refractive power, and a third lens group having a positive refractive power. A lens surface positioned nearest to an image side in the second lens group is a concave surface which is directed toward the image side. The second lens group moves along an optical axis.

7 Claims, 22 Drawing Sheets

(56) References Cited

U.S. PATENT DOCUMENTS

2016/0370558 A1  12/2016  Fakato
2017/0038570 A1   2/2017  Fakato

FOREIGN PATENT DOCUMENTS

WO    2016006486 A1    1/2016
WO    2016084494 A1    6/2016

OTHER PUBLICATIONS

International Preliminary Report on Patentability (IPRP) dated Jul. 11, 2019, and English-language translation of a Written Opinion issued in International Application No. PCT/JP2017/047131.
International Search Report (ISR) dated Jul. 10, 2018 issued in International Application No. PCT/JP2017/047131.
Written Opinion dated Jul. 10, 2018 issued in International Application No. PCT/JP2017/047131.
Chinese Office Action (and English language translation thereof) dated Apr. 26, 2021, issued in counterpart Chinese Application No. 201780071769.4.

* cited by examiner

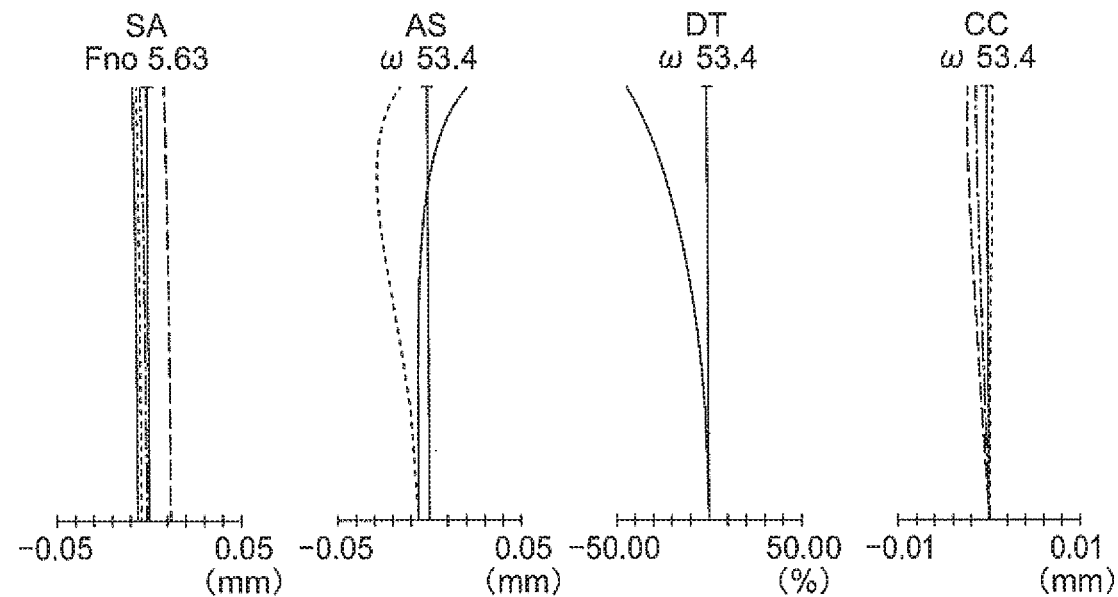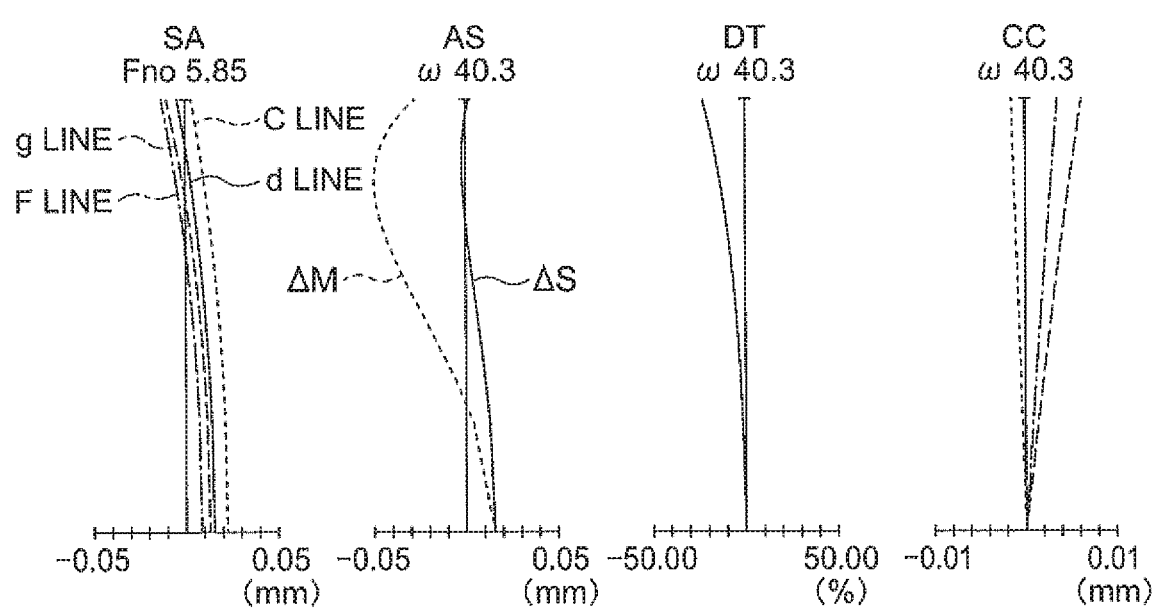

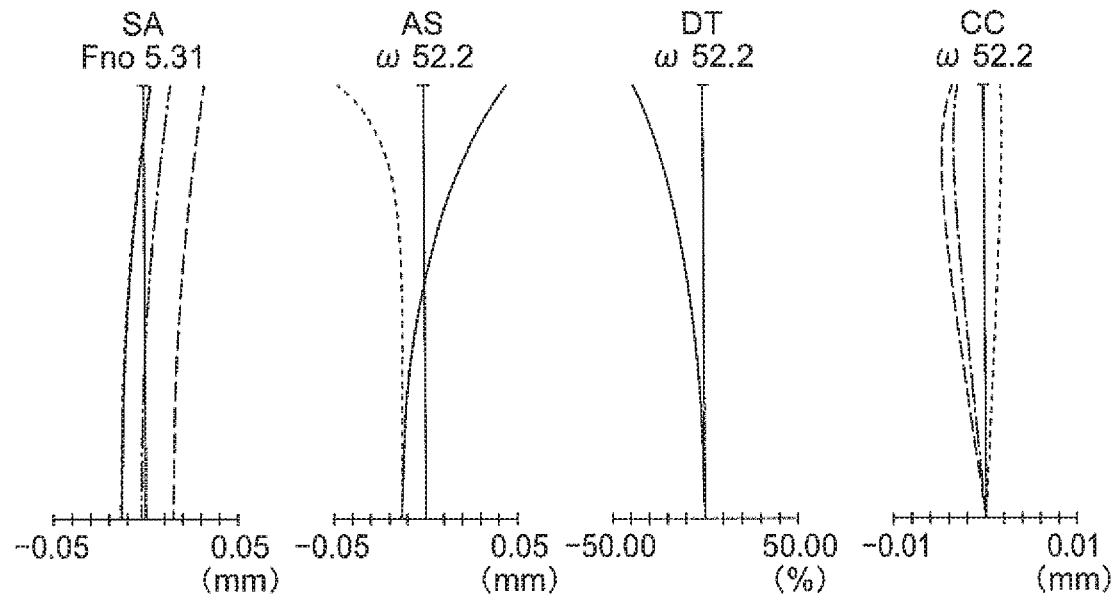
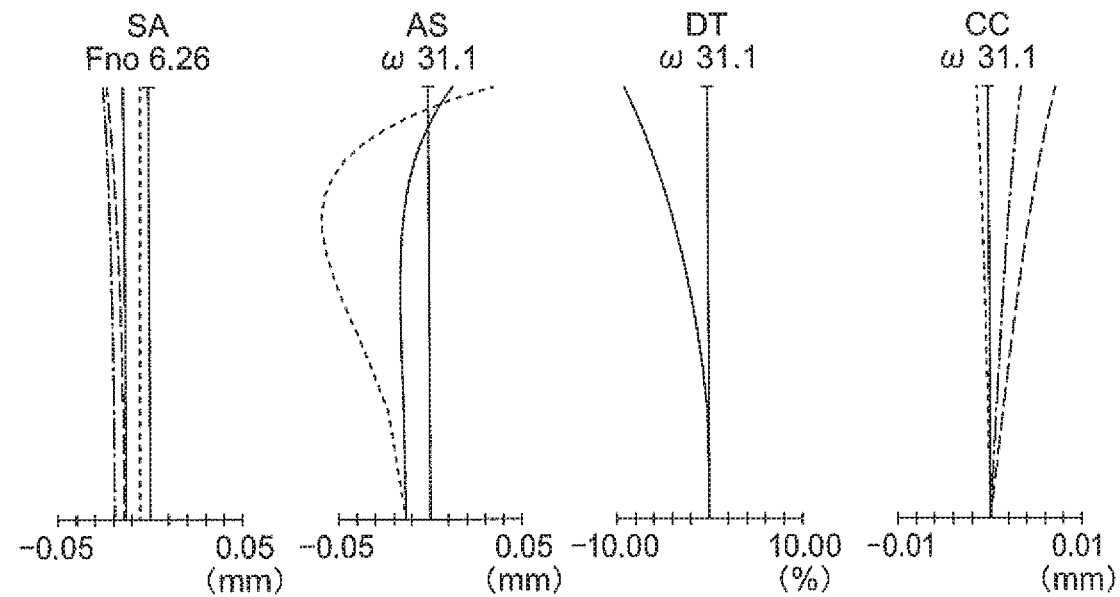

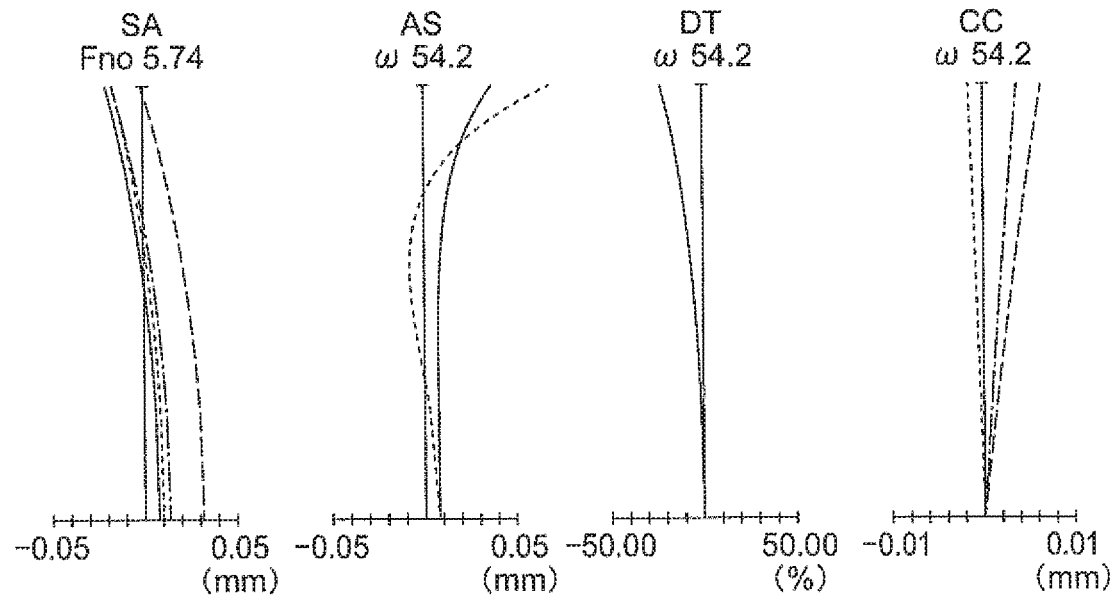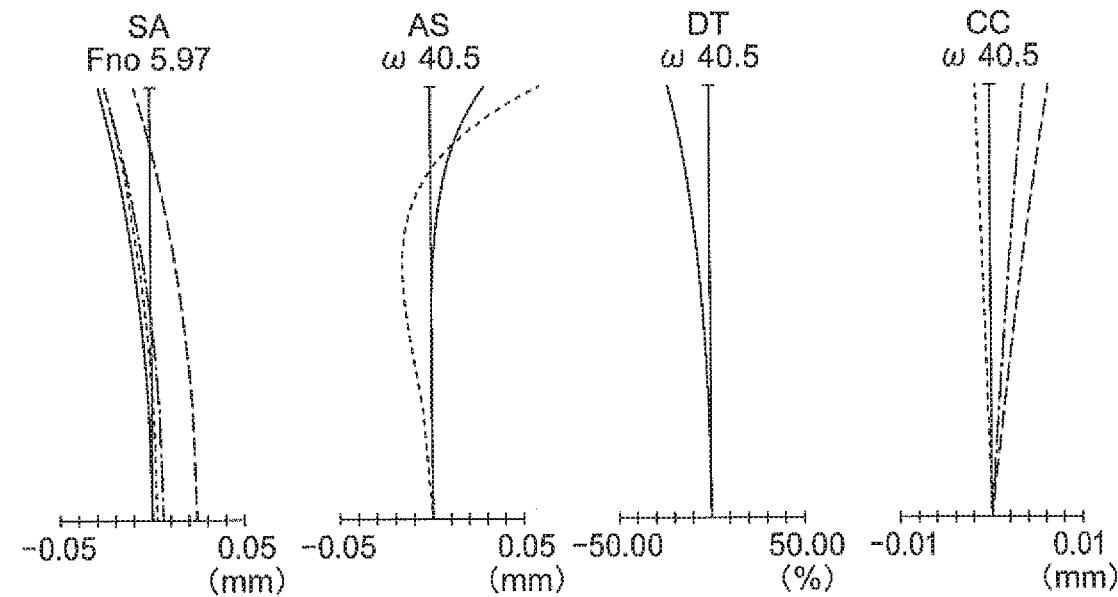

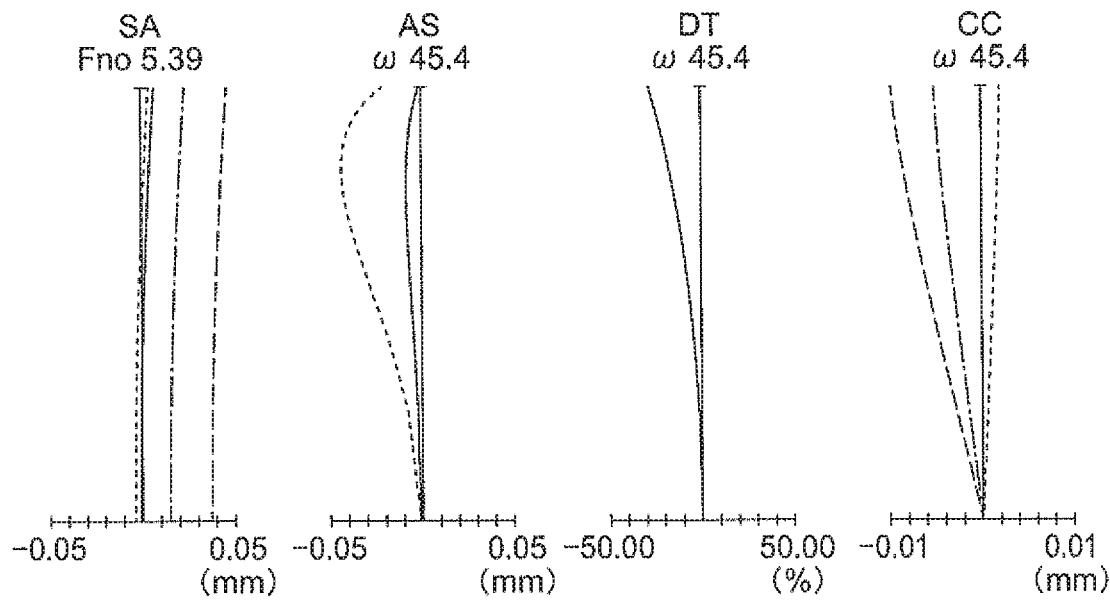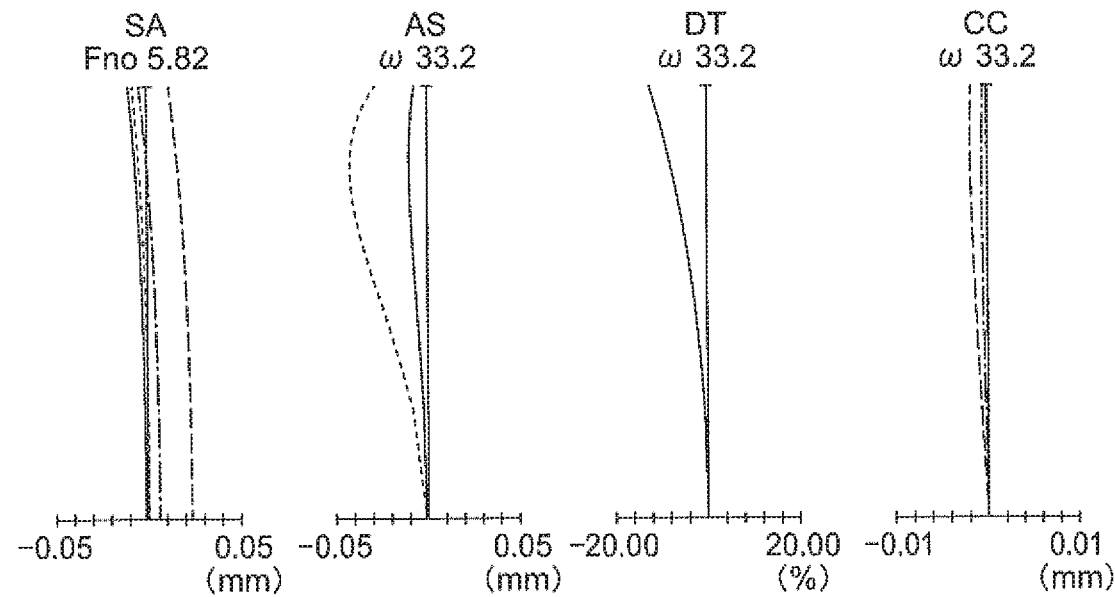

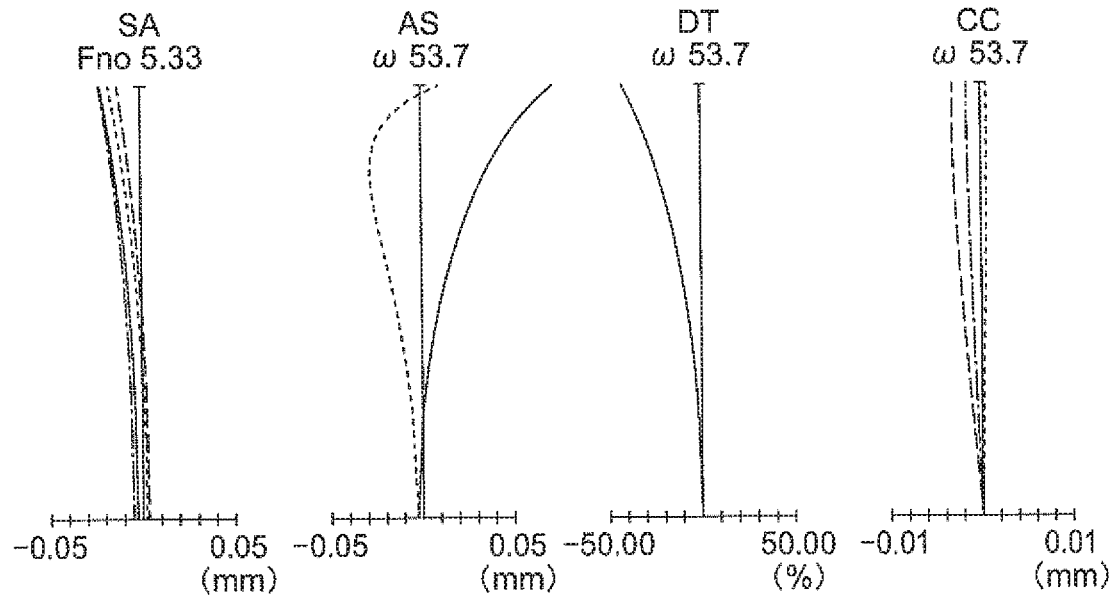
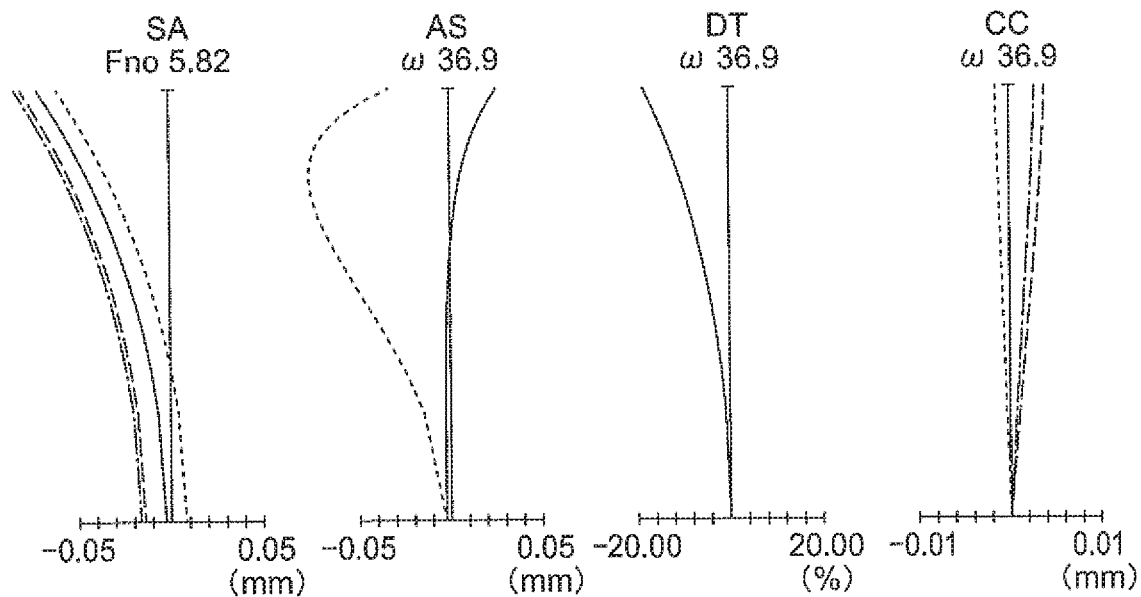

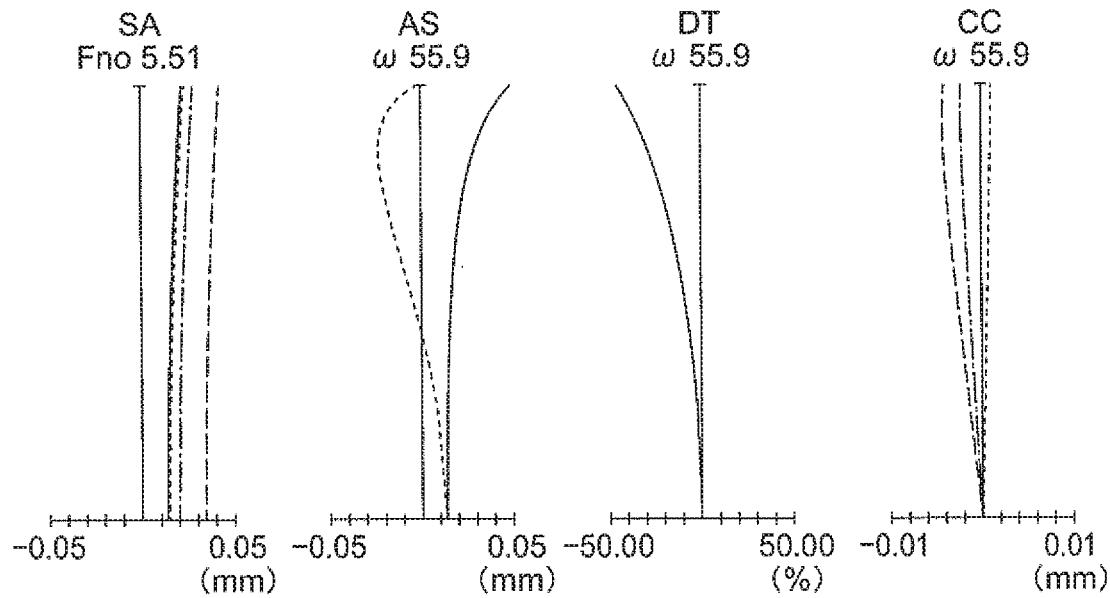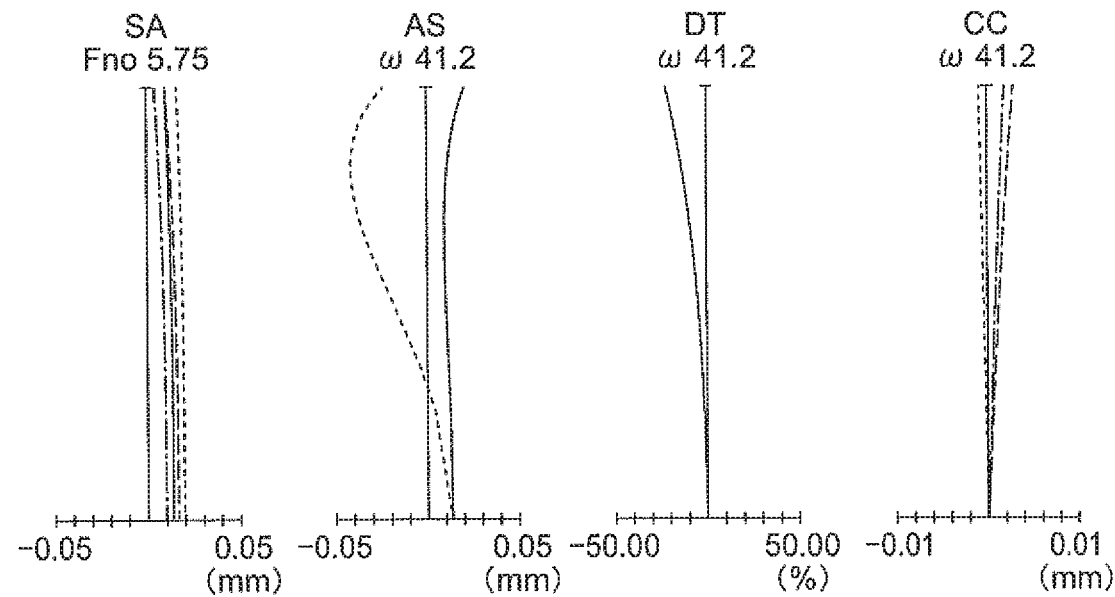

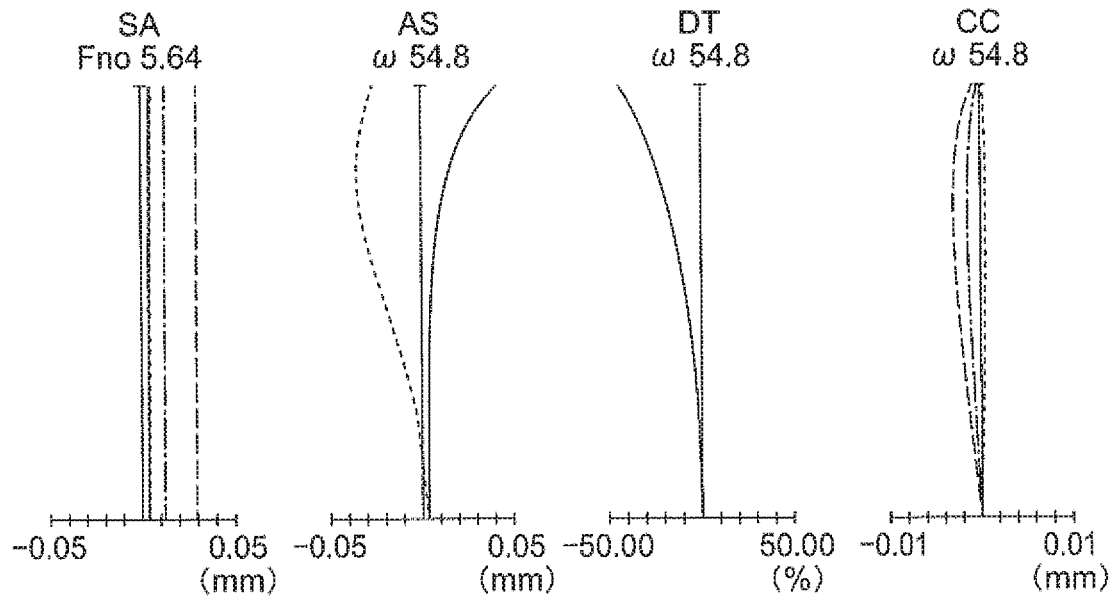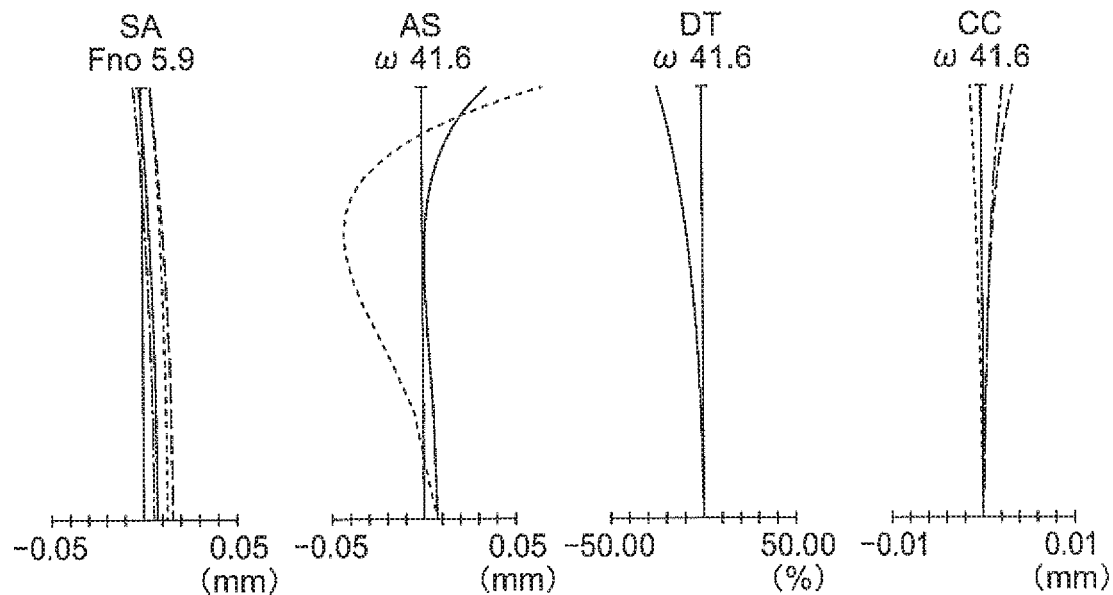

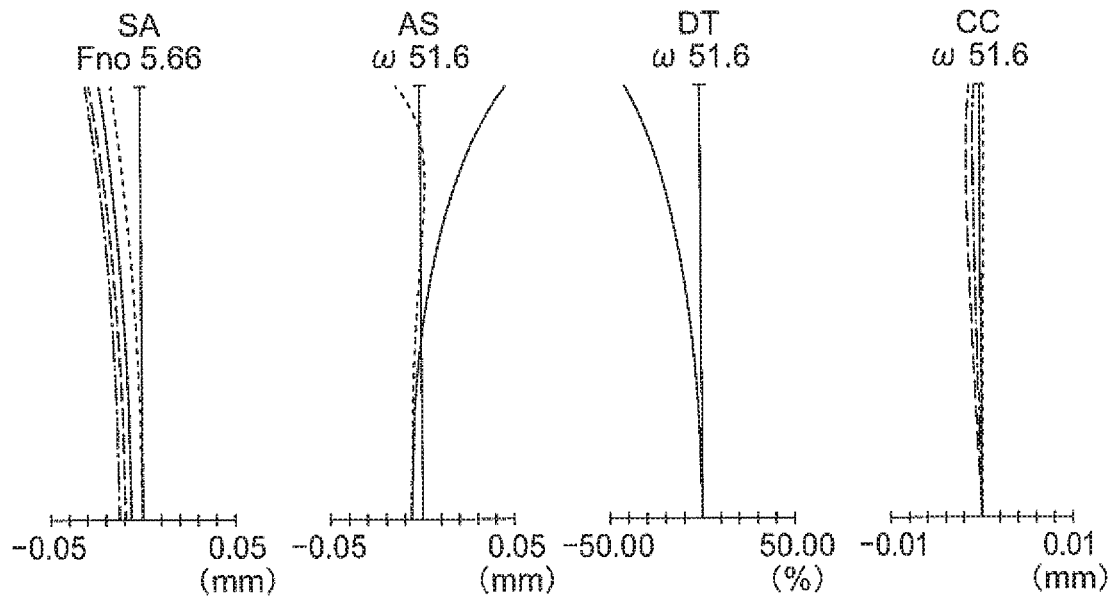
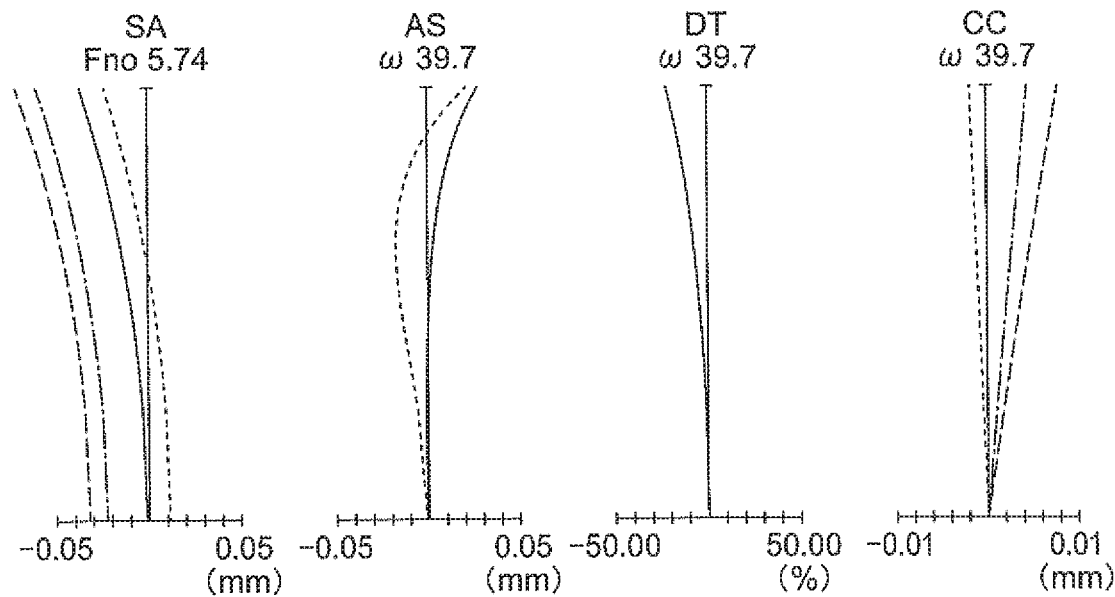

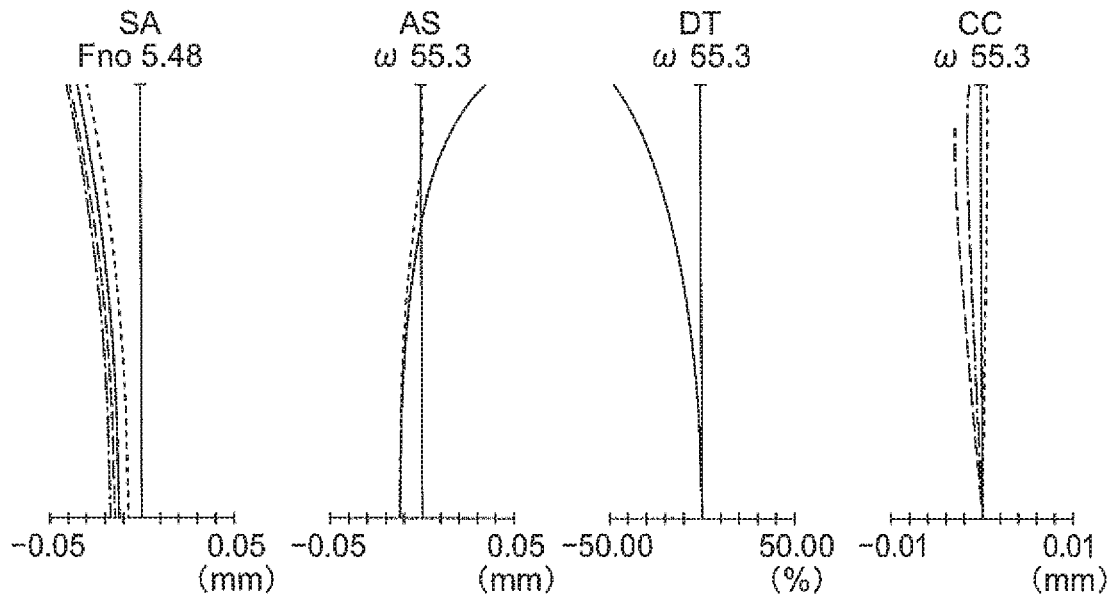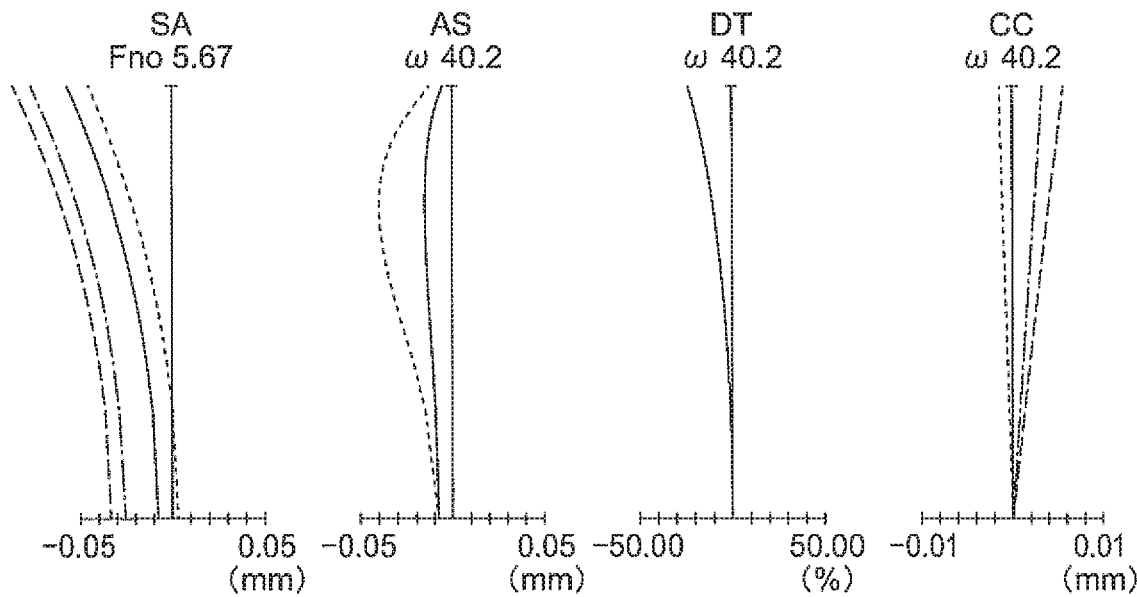

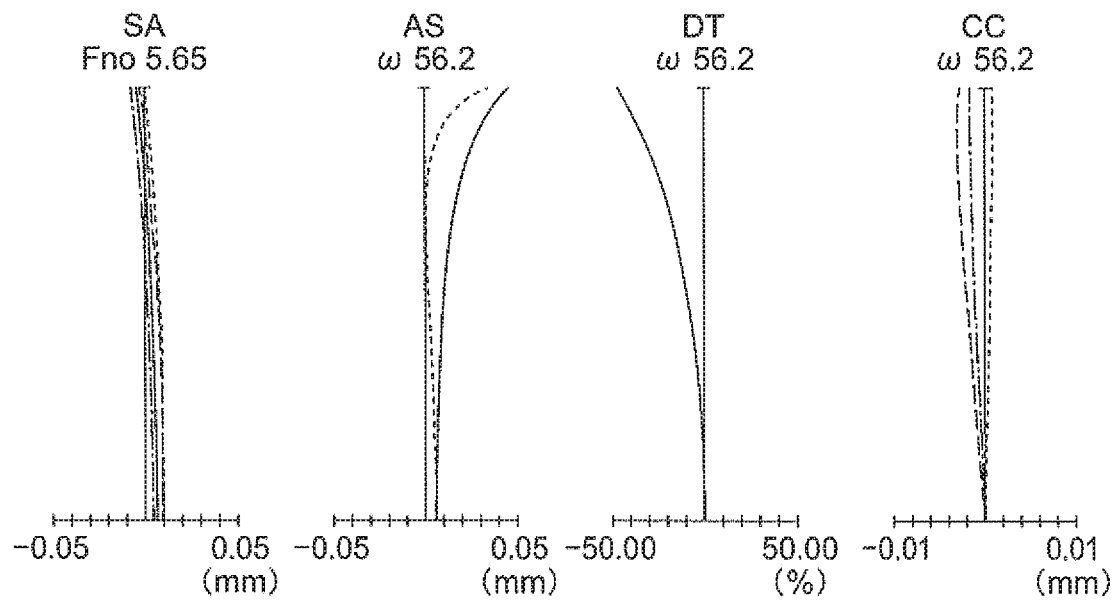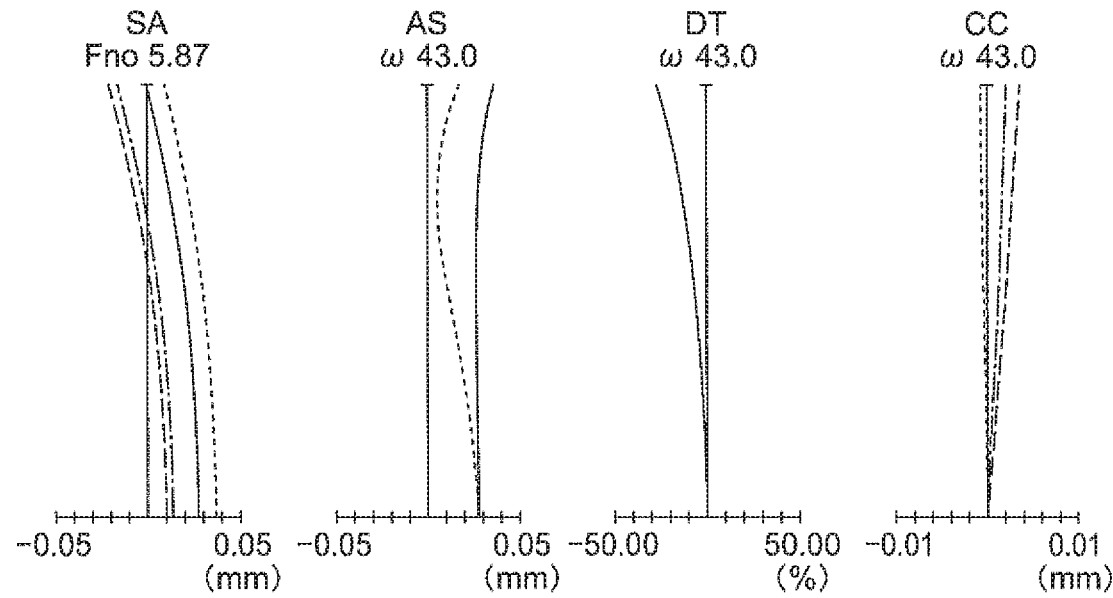

ENDOSCOPE OBJECTIVE OPTICAL SYSTEM

CROSS-REFERENCE TO RELATED APPLICATION

The present application is a continuation application of PCT/JP2017/047131 filed on Dec. 27, 2017 which is based upon and claims the benefit of priority from Japanese Patent Application No. 2016-255818 filed on Dec. 28, 2016; the entire contents of which are incorporated herein by reference.

BACKGROUND OF THE INVENTION

Field of the Invention

The present invention relates to an endoscope objective optical system.

Description of the Related Art

Magnified observation is a necessity of an endoscope. Particularly, in otorhinolaryngology and craniocervical surgery, the necessity of magnified observation is on rise in recent years.

In the otorhinolaryngology and the craniocervical surgery, there are expectations that detection of a precancerous lesion is made possible. For making the detection of a precancerous lesion possible, it is necessary to carry out an observation of capillary blood vessels on a surface of larynx and capillary blood vessels on a surface of pharynx. More specifically, a flow of blood in a capillary blood vessel is to be observed, and a state of the flow of blood is to be identified. By doing so, the detection of a precancerous lesion can be made possible However, capillary blood vessels are extremely thin. Therefore, magnified observation is necessary for observing the flow of blood. For such reason, a magnifying optical system with a high magnification becomes necessary for an endoscope to be used for the otorhinolaryngology and the craniocervical surgery.

Moreover, the magnified observation is used for purposes other than detection of a precancerous lesion. For instance, in a diagnosis of various lesion parts, it is necessary to observe the lesion parts minutely. Therefore, the magnified observation is used even for the diagnosis of lesion parts.

In a medical endoscope, for observing the body cavity, a long and slender insertion portion is inserted into a body cavity. The insertion portion has to be steered in various directions in the body cavity. For steering the insertion portion without causing an injury to a tissue in the body cavity, it is necessary to determine a direction of steering the insertion portion. Therefore, an optical system with a wide angle is sought for a medical endoscope.

Moreover, an observation range being narrow in the magnified observation, it is not easy to identify an object to be observed in the magnified observation. Therefore, a capability to observe a range wider than the observation range in the magnified observation becomes necessary. Even for such reason, an optical system with a wide angle is sought for a medical endoscope.

In the magnified observation, a distance from an objective lens up to an object position (hereinafter, referred to as 'object distance') is about 1 mm to 4 mm. Whereas, in the observation of a wide range as mentioned above (hereinafter, referred to as 'normal observation'), the object distance is much longer than 4 mm.

An endoscope objective lens which enables the magnified observation and the normal observation is disclosed in Japanese Patent Publication No. 4834799. The endoscope objective lens in Japanese Patent Publication No. 4834799 includes a first group having a positive refractive power, a second group having a negative refractive power, and a third group having a positive refractive power, and the second group moves.

SUMMARY OF THE INVENTION

An endoscope objective optical system according to at least some embodiments of the present invention consists of in order from an object side:

a first lens group having a positive refractive power,
a second lens group having a negative refractive power, and
a third lens group having a positive refractive power,
wherein
a lens surface positioned nearest to an image side in the second lens group is a concave surface which is directed toward the image side,
the second lens group moves along an optical axis, and
following conditional expressions (1) and (3) are satisfied:

$$-2.1 < f2/fW < -1 \quad (1)$$

$$0.45 < \Sigma d2/D2 < 0.64 \quad (3)$$

where,
f2 denotes a focal length of the second lens group,
fW denotes a focal length of the overall endoscope objective optical system at a time of a normal observation,
$\Sigma d2$ denotes a thickness of the second lens group, and
D2 denotes a distance from a lens surface positioned nearest to the image side in the first lens group up to a lens surface positioned nearest to an object side in the third lens group.

Moreover, another endoscope objective optical system according to at least some embodiments of the present invention consists of in order from an object side:

a first lens group having a positive refractive power,
a second lens group having a negative refractive power, and
a third lens group having a positive refractive power,
wherein
the second lens group consists of in order from the object side, a front group, an aperture stop, and a rear group,
a lens surface positioned nearest to the object side in the second lens group is a concave surface which is directed toward the object side,
a lens surface positioned nearest to an image side in the second lens group is a concave surface which is directed toward the image side, and
the second lens group moves along an optical axis.

BRIEF DESCRIPTION OF THE DRAWINGS

FIG. 4A, FIG. 4B, FIG. 4C, FIG. 4D, FIG. 4E, FIG. 4F, FIG. 4G, and FIG. 4H are aberration diagrams of the endoscope objective optical system of the example 1;

FIG. 6A, FIG. 6B, FIG. 6C, FIG. 6D, FIG. 6E, FIG. 6F, FIG. 6G, and FIG. 6H are aberration diagrams of the endoscope objective optical system of the example 2;

FIG. 8A, FIG. 8B, FIG. 8C, FIG. 8D, FIG. 8E, FIG. 8F, FIG. 8G, and FIG. 8H are aberration diagrams of the endoscope objective optical system of the example 3;

FIG. 10A, FIG. 10B, FIG. 10C, FIG. 10D, FIG. 10E, FIG. 10F, FIG. 10G, and FIG. 10H are aberration diagrams of the endoscope objective optical system of the example 4;

FIG. 12A, FIG. 12B, FIG. 12C, FIG. 12D, FIG. 12E, FIG. 12F, FIG. 12G, and FIG. 12H are aberration diagrams of the endoscope objective optical system of the example 5;

FIG. 14A, FIG. 14B, FIG. 14C, FIG. 14D, FIG. 14E, FIG. 14F, FIG. 14G, and FIG. 14H are aberration diagrams of the endoscope objective optical system of the example 6;

FIG. 16A, FIG. 16B, FIG. 16C, FIG. 16D, FIG. 16E, FIG. 16F, FIG. 16G, and FIG. 16H are aberration diagrams of the endoscope objective optical system of the example 7;

FIG. 18A, FIG. 18B, FIG. 18C, FIG. 18D, FIG. 18E, FIG. 18F, FIG. 18G, and FIG. 18H are aberration diagrams of the endoscope objective optical system of the example 8;

FIG. 20A, FIG. 20B, FIG. 20C, FIG. 20D, FIG. 20E, FIG. 20F, FIG. 20G, and FIG. 20H are aberration diagrams of the endoscope objective optical system of the example 9;

FIG. 22A, FIG. 22B, FIG. 22C, FIG. 22D, FIG. 22E, FIG. 22F, FIG. 22G, and FIG. 22H are aberration diagrams of the endoscope objective optical system of the example 10.

DETAILED DESCRIPTION OF THE INVENTION

Figure 1A:
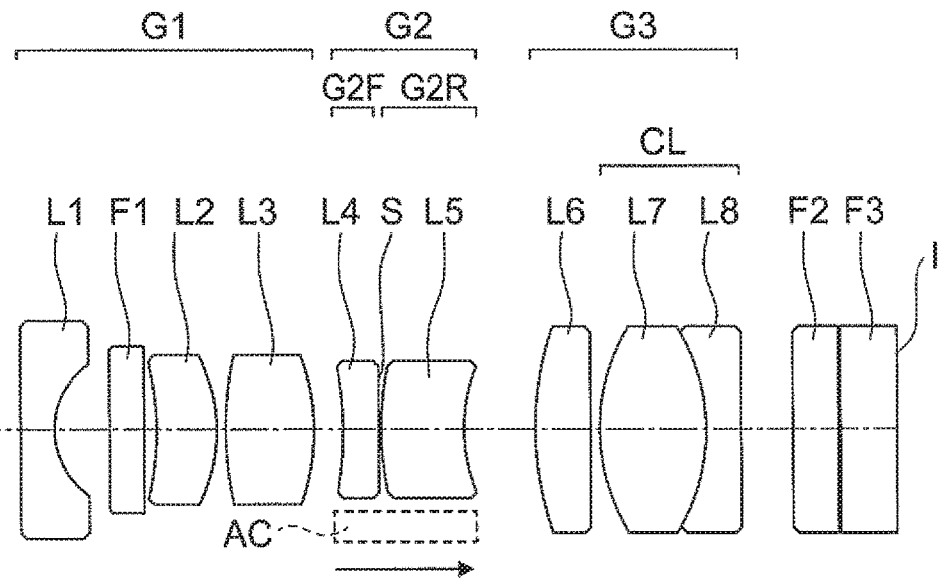
FIG. 1A and FIG. 1B are lens cross-sectional views showing a lens arrangement of an endoscope objective optical system according to the present embodiment.

Reasons for adopting such arrangements and effects thereof in an endoscope objective optical system according to the present embodiment, will be described below by referring to the accompanying diagrams. However, the present invention is not restricted to the endoscope objective optical system according to the following embodiment.

An endoscope objective optical system according to the present embodiment includes in order from an object side, a first lens group having a positive refractive power, a second lens group having a negative refractive power, and a third lens group having a positive refractive power, wherein a lens surface positioned nearest to an image side in the second lens group is a concave surface which is directed toward the image side, and the second lens group moves along an optical axis.

In the endoscope objective optical system according to the present embodiment, it is preferable that the following conditional expressions (1) and (3) be satisfied:

$$-2.1 < f2/fW < -1 \quad (1)$$

$$0.45 < \Sigma d2/D2 < 0.64 \quad (3)$$

where, f2 denotes a focal length of the second lens group, fW denotes a focal length of the overall endoscope objective optical system at a time of a normal observation, Σd2 denotes a thickness of the second lens group, and D2 denotes a distance from a lens surface positioned nearest to the image side in the first lens group up to a lens surface positioned nearest to an object side in the third lens group.

A technical significance of an arrangement of the optical system and a technical significance of conditional expressions will be described later.

Moreover, an endoscope objective optical system according to the present embodiment includes in order from an object side, a first lens group having a positive refractive power, a second lens group having a negative refractive power, and a third lens group having a positive refractive power, wherein the second lens group includes in order from the object side, a front group, an aperture stop, and a rear group, a lens surface positioned nearest to the object side in the second lens group is a concave surface which is directed toward the object side, a lens surface positioned nearest to an image side in the second lens group is a concave surface which is directed toward the image side, and the second lens group moves along an optical axis.

In the endoscope objective optical system according to the present embodiment, a normal observation and a magnified observation can be carried out. In the normal observation, a wide range is observed with a low magnification, and in the magnified observation, a narrow range is observed with a high magnification. Accordingly, the endoscope objective optical system is required to have a favorable imaging performance in both the normal observation and the magnified observation.

In the endoscope objective optical system according to the present embodiment, the optical system includes in order from the object side, the first lens group having a positive refractive power, the second lens group having a negative refractive power, and the third lens group having a positive refractive power. By making such arrangement, not only it is possible to correct an aberration favorably but also it becomes easy to realize a small-sizing of the overall optical system.

Figure 1B:
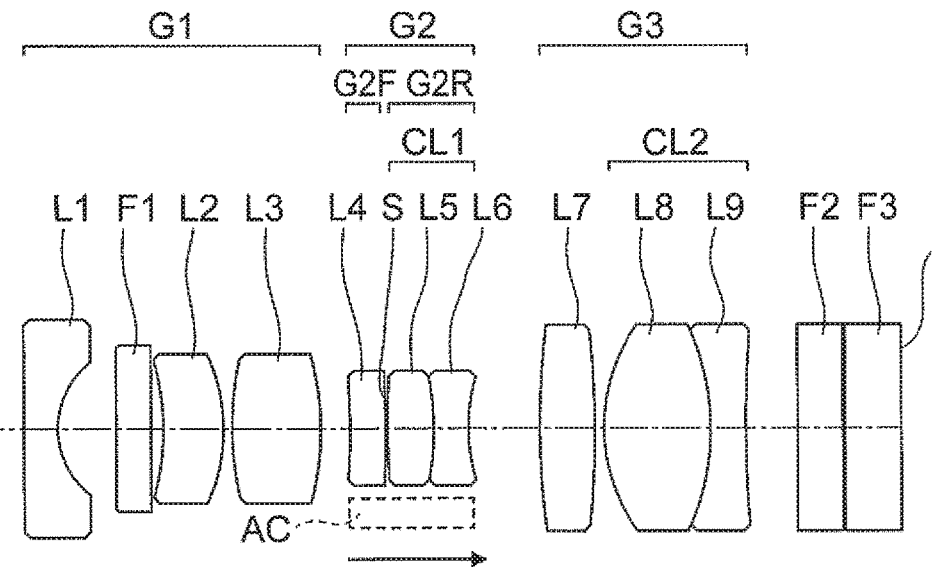

FIG. 1A and FIG. 1B are lens cross-sectional views showing a specific arrangement of the endoscope objective optical system according to the present embodiment, where, FIG. 1A is a cross-sectional view of an endoscope objective optical system according to a first embodiment, and FIG. 1B is a cross-sectional view of an endoscope objective optical system according to a second embodiment.

The endoscope objective optical system according to the first embodiment includes in order from an object side, a first lens group G1 having a positive refractive power, a second lens group G2 having a negative refractive power, and a third lens group G3 having a positive refractive power. An aperture stop S is disposed in the second lens group G2.

The first lens group G1 includes in order from the object side, a first lens L1 having a negative refractive power, a second lens L2 having a positive refractive power, and a third lens L3 having a positive refractive power.

The second lens group G2 includes in order from the object side, a front group G2F, the aperture stop S, and a rear group G2R. The front group G2F includes a fourth lens L4 having a negative refractive power. The rear group G2R includes a fifth lens L5 having a negative refractive power. An object-side lens surface of the fourth lens L4 is positioned nearest to the object side, and a concave surface is directed toward the object side. An image-side lens surface of the fifth lens L5 is positioned nearest to the image side, and a concave surface is directed toward the image side.

The third lens group G3 includes in order from the object side, a sixth lens L6 having a positive refractive power, a seventh lens L7 having a positive refractive power, and an eighth lens L8 having a negative refractive power. The seventh lens L7 and the eighth lens L8 are cemented, and form a cemented lens CL.

The endoscope objective optical system according to the second embodiment includes in order from an object side, a first lens group G1 having a positive refractive power, a second lens group G2 having a negative refractive power, and a third lens group G3 having a positive refractive power. An aperture stop S is disposed in the second lens group G2.

The first lens group G1 includes in order from the object side, a first lens L1 having a negative refractive power, a second lens L2 having a positive refractive power, and a third lens L3 having a positive refractive power.

The second lens group G2 includes in order from the object side, a front group G2F, the aperture stop S, and a rear group G2R. The front group G2F includes a fourth lens L4 having a negative refractive power. The rear group G2R includes a fifth lens L5 having a positive refractive power and a sixth lens L6 having a negative refractive power. The fifth lens L5 and the sixth lens L6 are cemented, and form a cemented lens CL1. An object-side lens surface of the fourth lens L4 is positioned nearest to the object side, and a concave surface is directed toward the object side. An image-side lens surface of the sixth lens L6 is positioned nearest to the image side, and a concave surface is directed toward an image side.

The third lens group G3 includes in order from the object side, a seventh lens L7 having a positive refractive power, an eighth lens L8 having a positive refractive power, and a ninth lens L9 having a negative refractive power. The eighth lens L8 and the ninth lens L9 are cemented, and form a cemented lens CL2.

In the endoscope objective optical system according to the first embodiment and the endoscope objective optical system according to the second embodiment (hereinafter, referred to as 'the endoscope objective optical system according to the embodiment'), a first plane parallel plate F1 is disposed between the first lens L1 and the second lens L2. It is possible to dispose the first plane parallel plate F1 at an arbitrary position in the endoscope objective optical system. A second plane parallel plate F2 and a third plane parallel plate F3 are disposed on the image side of the ninth lens L9. The second plane parallel plate F2 and the third plane parallel plate F3 are cemented.

The second plane parallel plate F2 is a cover glass. The third plane parallel plate F3 is an imager glass. An image pickup element (not shown in the diagram) is disposed on the image side of the third plane parallel plate F3. An image-side surface of the third plane parallel plate F3 is an image plane I. An image pickup surface of the image pickup element coincides with the image-side surface of the third plane parallel plate F3.

In the endoscope objective optical system according to the present embodiment, the second lens group G2 includes in order from the object side, the front group G2F, the aperture stop S, and the rear group G2R.

Figure 2A:
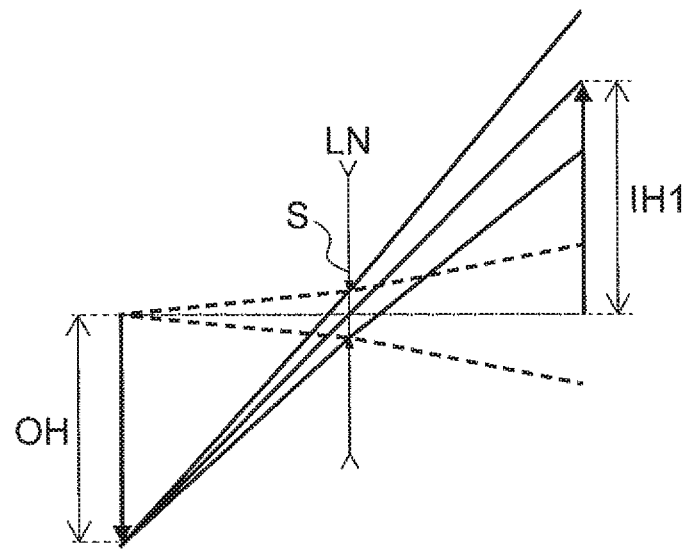
FIG. 2A and FIG. 2B are diagrams showing an appearance of an axial light ray and an appearance of an off-axis light ray.
Figure 2B:
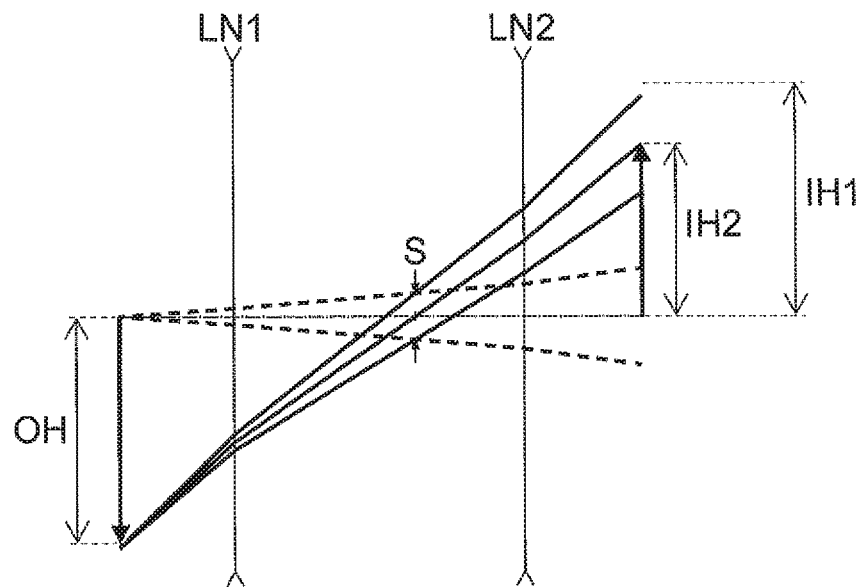

An arrangement of the second lens group G2 will be described below. FIG. 2A and FIG. 2B are diagrams showing an appearance of an axial light ray and an appearance of an off-axis light ray, where FIG. 2A is a diagram showing an appearance of a light ray in a first arrangement and FIG. 2B is a diagram showing an appearance of a light ray in a second arrangement.

In each diagram, an arrangement of the second lens group is depicted in a simplified manner. Moreover, the axial light ray is indicated by dashed lines, and the off-axis light ray is indicated by solid lines. These light rays are light rays when a height of an object is 1 mm, and a focal length of the second lens group G2 is 1 mm. A magnification ratio in the first arrangement and a magnification ratio in the second arrangement are same.

Moreover, in each diagram, OH denotes an object height. More specifically, the object height is 1 mm. An image of the object is a virtual image. In the diagrams, IH1 denotes an image height in the first arrangement and IH2 denotes an image height in the second arrangement. Moreover, IH1 and IH2 are heights at a position becoming a back focus.

The second lens group G2 has an effect of negative refraction as a whole, and moreover, a paraxial image formation is realized therein. In this case, when only an axial image formation (image formation in a paraxial area) is taken into consideration, and moreover, when the second lens group G2 is indicated by a thin lens, the arrangement of the second lens group G2, as shown in FIG. 2A, becomes an arrangement (hereinafter, referred to as 'first arrangement') in which one negative lens LN is disposed near the aperture stop S.

Although it is omitted in the diagram, the first lens group G1 is positioned on the object side of the negative lens LN, and the third lens group G3 is positioned on the image side of the negative lens LN. Taking the off-axis light ray into account, in the first arrangement, the light ray height becomes high both on the first lens group G1 side and the third lens group G3 side.

Therefore, the effect of negative refraction in the second lens group G2 is to be divided. More specifically, the second lens group G2 includes the front group G2F and the rear group G2R. When each of the front group G2F and the rear group G2R is indicated by a thin lens, the arrangement of the second lens group G2, as shown in FIG. 2B, becomes an arrangement in which both of a negative lens LN1 and a negative lens LN2 are disposed at positions distant from the aperture stop S (hereinafter, referred to as 'second arrangement').

In the second arrangement, both the height of a light ray at the negative lens LN1 and the light of a light ray at the negative lens LN2 become low. In other words, according to the second arrangement, both the height of an off-axis light ray incident on a lens surface of the front group G2F and the height of an off-axis light ray incident on a lens surface of the rear group G2R become low. As a result, it is possible to lower the height of a light ray at the lens surface on the first lens group G1 side and the height of a light ray at the lens surface on the third lens group G3 side.

Moreover, in the second arrangement, since the height of an off-axis light ray becomes low, IH2 becomes smaller than IH1 (IH2<IH1).

Practically, a lens has a thickness. Therefore, in the front group G2F, a lens surface positioned nearest to the object side is a concave surface directed toward the object side, and in the rear group G2R, a lens surface positioned nearest to the image side is a concave surface directed toward the image side. By making such arrangement, it is possible to make the height of a light ray at the second lens group G2 low. As a result, it is possible to make a diameter of the second lens group adequately small.

For instance, it is possible to make the lens positioned nearest to the object side a planoconcave lens in the front group G2F and to make the lens positioned nearest to the image side in the rear lens group G2R a planoconcave lens. Moreover, it is preferable to dispose the two planoconcave lenses such that flat surfaces are positioned on the aperture stop S side.

In the endoscope objective optical system of the present embodiment, the normal observation and the magnified observation are carried out. The focal length differs for the normal observation and the magnified observation. In switch-over between the normal observation and the magnified observation, it is preferable that a sharp image be formed even when the focal length varies. For this, it is necessary that at least one lens group moves along an optical axis.

In a case in which an endoscope objective optical system includes a plurality of lens groups, the lens group to be moved for focusing may be any lens group. Moreover, the number of the lens groups to be moved may be one or in plurality.

However, in a case of moving the entire endoscope objective optical system, all the lens groups are to be moved. In this case, weight of the lens groups to be moved becomes heavy. Consequently, a load exerted on a drive mechanism becomes heavy. Moreover, the drive mechanism also becomes large in size. Therefore, it is not preferable to move all the lens groups.

Moreover, even in a case of moving a plurality of lens groups, the load exerted on the drive mechanism becomes heavier as compared to that in a case of moving one lens group, and also, the drive mechanism becomes large in size.

For such reason, it is preferable that the number of lens groups to be moved be small. When the number of lens groups to be moved is one, an effect that it is possible to simplify the drive mechanism is exerted.

Moreover, it is also possible to keep the lens group fixed, and instead, to move an image pickup element. However, even in a case of moving the image pickup element, the drive mechanism becomes necessary. In a case of moving the image pickup element, a structure of the drive mechanism becomes complicated. Consequently, a weight of the drive mechanism becomes heavy. Moreover, the load exerted on the drive mechanism also becomes heavy, and furthermore, the drive mechanism also becomes large in size. Therefore, it is not preferable to move the image pickup element.

The drive mechanism is disposed around the endoscope objective optical system. As mentioned above, in the endoscope objective optical system of the present embodiment, the diameter of the second lens group has been made adequately thin. Therefore, as shown in FIG. 1A and FIG. 1B, in the endoscope objective optical system according to the present embodiment, it is possible to dispose a drive mechanism. AC near the second lens group G2. As a result, it is possible to prevent the diameter of the insertion portion from becoming thick. Moreover, the number of lens groups to be moved being one, it is possible to simplify the drive mechanism.

As the drive mechanism AC, it is possible to use a linear actuator for example. The linear actuator has a soft magnetic body, a permanent magnet, and a coil. The permanent magnet and the coil are disposed concentrically in a peripheral portion of the soft magnetic body.

The linear actuator is an element in which a variation of magnetic field due to an electromagnetic induction is used. In the linear actuator, a change in the magnetic field is caused by changing a current to the coil, and the soft magnetic body, or in other words, a target object is moved by a magnetic force.

While moving the second lens group G2, it is preferable to move the front group G2F, the aperture stop S, and the rear group G2R integrally. In this case, a distance between the front group G2F and the aperture stop S and a distance between the aperture stop S and the rear group G2R are same at the time of normal observation and at the time of magnified observation.

In other words, while the second lens group G2 moves, the distance between the front group G2F and the aperture stop S and the distance between the aperture stop S and the rear group G2R do not change at all. Therefore, it is possible to further simplify the drive mechanism.

However, an arrangement may be made such that the distance between the front group G2F and the aperture stop S and the distance between the aperture stop S and the rear group G2R change at the time of the normal observation and at the time of the magnified observation.

In the endoscope objective optical system according to the present embodiment, it is preferable that the following conditional expressions (1), (2), and (3) be satisfied:

$$-2.1 < f2/fW < -1 \quad (1)$$

$$-37 < f2F/f2 < 19 \quad (2)$$

$$0.45 < \Sigma d2/D2 < 0.64 \quad (3)$$

where, f2 denotes a focal length of the second lens group, fW denotes a focal length of the overall endoscope objective optical system at the time of normal observation, f2F denotes a focal length of the front group, $\Sigma d2$ denotes a thickness of the second lens group, and D2 denotes a distance from a lens surface positioned nearest to the image side in the first lens group up to a lens surface positioned nearest to the object side in the third lens group.

Conditional expression (1) is a conditional expression related to a ratio of the focal length of the second lens group and the focal length of the overall endoscope objective optical system at the time of normal observation.

In a case of falling below a lower limit value of conditional expression (1), an angle of view becomes excessively large. In this case, a height of a light ray at the first lens group or a height of a light ray at the second lens group becomes high. Consequently, it leads to an increase in an outer diameter of lenses in the optical system, or in other words, an increase in size of the optical system in a radial direction. Therefore, it is not preferable to fall below the lower limit value of conditional expression (1).

In a case of exceeding an upper limit value of conditional expression (1), it is not possible to secure the angle of view adequately. Consequently, at the time of normal observation, it is not possible to observe a wide range.

Conditional expression (2) is a conditional expression related to a ratio of the focal length of the front group and the focal length of the second lens group.

In a case of falling below a lower limit value of conditional expression (2), the effect of negative refraction at the front group becomes excessively small. In this case, since it is necessary to maintain the negative refractive power of the overall second lens group to be appropriate, the effect of negative refraction at a lens surface positioned nearest to the image side in the rear group becomes large. As a result, it causes an excessive curvature of field. Therefore, it is not preferable to fall below the lower limit value of conditional expression (2).

In a case of exceeding an upper limit value of conditional expression (2), one of a height of a light ray at the second lens group and a height of a light ray at the third lens group becomes high. In this case, as a result, it leads to an increase in size of the optical system in a radial direction. Therefore, it is not preferable to exceed the upper limit value of conditional expression (2).

Conditional expression (3) is a conditional expression related to a ratio of the thickness of the second lens group and the distance from the first lens group up to the third lens group. The thickness of the second lens group is an absolute value of a distance from a lens surface positioned nearest to the object side in the second lens group up to a lens surface positioned nearest to the image side in the second lens group. Moreover, the distance from the first lens group up to the third lens group is an absolute value of a distance from a lens surface positioned nearest to the image side in the first lens group up to a lens surface positioned nearest to the object side in the third lens group.

In a case of falling below a lower limit value of conditional expression (3), both a height of a light ray on the image side of the first lens group and a height of a light ray on the object side of the third lens group become high. Consequently, it leads to an increase in size of the optical system in the radial direction. Accordingly, it is not preferable to fall below the lower limit value of conditional expression (3).

In a case of exceeding an upper limit value of conditional expression (3), an angle of incidence of a principal light ray on an image plane becomes large. In this case, when the second lens group, in particular, is moved toward the image side, it leads to a reduction of a quantity of light off-axially. In other words, at the time of magnified observation, a peripheral portion of an image becomes dark. Therefore, it is not preferable to exceed the upper limit value of conditional expression (3).

In the endoscope objective optical system according to the present embodiment, it is preferable that the second lens group include at least one predetermined lens, the predetermined lens be a planoconcave lens or a meniscus lens, and the following conditional expression (4) be satisfied:

$$1.85 < N2 \quad (4)$$

where,

N2 denotes a refractive index for an e-line of the predetermined lens.

The second lens group has an arrangement in which the front group is positioned on the object side and the rear group is positioned on the image side, sandwiching the aperture stop in between, and has a negative refractive power as a whole. By at least one of the front group and the rear group including the predetermined lens, it is possible to suppress a height of an off-axis light ray with a paraxial image formation maintained favorably as it has been. The predetermined lens is either a planoconcave lens or a meniscus lens.

Conditional expression (4) is a conditional expression related to the refractive index of the predetermined lens. As mentioned above, the predetermined lens is at least one of the planoconcave lens and the meniscus lens included in the second lens group.

Satisfying conditional expression (4) signifies that a glass material having a high refractive index is used for the predetermined lens. By making the refractive index of the glass material of the predetermined lens high, it is possible to shorten an air-conversion length of the second lens group. As a result, it is possible to lower the height of the off-axis light ray in the second lens group.

In a case of falling below a lower limit value of conditional expression (4), the height of the light ray at the first lens group or the height of the light ray at the third lens group becomes high. Therefore, it is not preferable to fall below the lower limit value of conditional expression (4).

In the endoscope objective optical system according to the present embodiment, it is preferable that the following conditional expression (5) be satisfied:

$$-0.55 < P2/fW < -0.22 \quad (5)$$

where,

P2 denotes Petzval's sum for the second lens group, and fW denotes the focal length of the overall endoscope objective optical system at the time of normal observation.

Conditional expression (5) is a conditional expression standardizing Petzval's sum for the second lens group by the focal length of the overall endoscope objective optical system at the time of normal observation.

In a case of falling below a conditional expression (5), the curvature of field becomes excessive. Therefore, it is not preferable to fall below the lower limit value of conditional expression (5). In a case of exceeding an upper limit value of conditional expression (5), a radius of curvature of a concave surface in the second lens group becomes large. As a result, correction of a spherical aberration becomes inadequate. Therefore, it is not preferable to exceed the upper limit value of conditional expression (5).

It is more preferable that the following conditional expression (5') be satisfied instead of conditional expression (5).

$$-0.45 < P2/fW < -0.27 \quad (5')$$

By satisfying conditional expression (5'), it is possible to correct the curvature of field and the spherical aberration favorably.

In the endoscope objective optical system of the present embodiment, it is preferable that the following conditional expression (6) be satisfied:

$$0.4 < \Sigma L2F/\Sigma L2R < 1.25 \quad (6)$$

where, $\Sigma L2F$ denotes a sum of an air-conversion length of lenses in the front group, and $\Sigma L2R$ denotes a sum of an air-conversion length of lenses in the rear group.

Conditional expression (6) is a conditional expression related to the sum of the air-conversion length of the lenses in the front group and the sum of the air-conversion length of the lenses in the rear group.

In a case of falling below a lower limit value of conditional expression (6), a practical distance between the aperture stop and the third lens group becomes long. In this case, the height of the light ray at the third lens group becomes high. Consequently, it leads to an increase in an outer diameter of lenses in the third lens group. Therefore, it is not preferable to fall below the lower limit value of conditional expression (6).

In a case of exceeding an upper limit value of conditional expression (6), a practical distance between the first lens group and the aperture stop becomes long. In this case, the height of the light ray at the first lens group becomes excessively high. Consequently, it leads to an increase in an outer diameter of lenses in the first lens group. Therefore, it is not preferable to exceed the upper limit value of conditional expression (6).

In the endoscope objective optical system of the present embodiment, a lens surface having a positive refractive power may be positioned near a surface of the aperture stop.

By making such arrangement, it is possible to impart a degree of freedom to the refractive power of the concave surface in the front group and the refractive power of the concave surface in the rear group, while maintaining an appropriate magnitude of the negative refractive power of the overall second lens group. As a result, it is possible to carry out easily a control of a thickness of the front group and a thickness of the rear group. Moreover, since it is possible to correct an off-axis aberration favorably, it is possible to make favorable an imaging performance around a peripheral portion of an image.

Making such arrangement is beneficial for an effect of control of a height of a light ray in the second lens group, and an effect of correction of the curvature of field and an effect of correction of the longitudinal chromatic aberration.

In the endoscope objective optical system of the present embodiment, the refractive power of the front group may be a positive refractive power.

By the front group having a positive refractive power, it is possible to achieve an effect similar to that in a case in which a lens surface having a positive refractive power is positioned near the surface of the aperture stop.

EXAMPLE 1

Figure 3A:
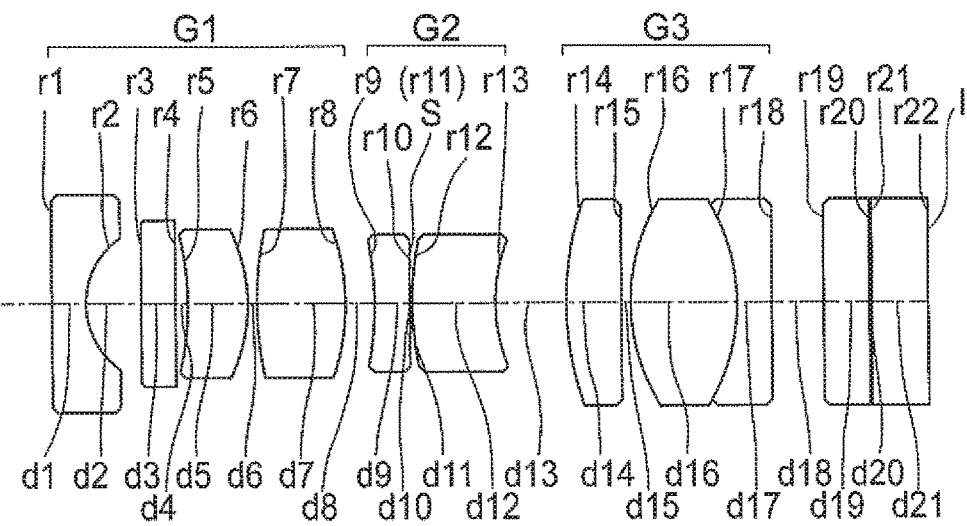
FIG. 3A and FIG. 3B are lens cross-sectional views of an endoscope objective optical system of an example 1.
Figure 3B:
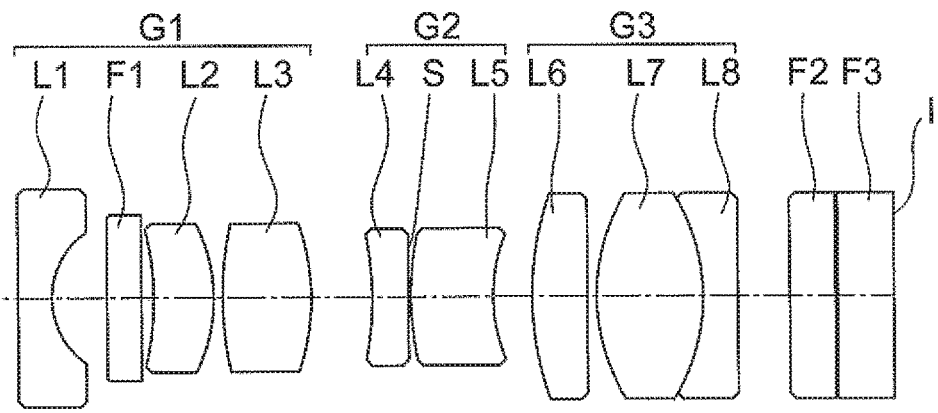

An endoscope objective optical system according to an example 1 will be described below. FIG. 3A and FIG. 3B are lens cross-sectional views of the endoscope objective optical system according to the example 1, where, FIG. 3A is a cross-sectional view in a normal observation state and FIG. 3B is a cross-sectional view in a magnified observation state.

The endoscope objective optical system of the example 1 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3. It is possible to use sapphire as a glass material of the planoconcave negative lens L1.

The second lens group G2 includes a planoconcave negative lens L4 of which an image side is a flat surface and a negative meniscus lens L5 having a convex surface directed toward the object side. The front group includes the planoconcave negative lens L4, and the rear group includes the negative meniscus lens L5.

An aperture stop S is disposed between the planoconcave negative lens L4 and the negative meniscus lens L5. More specifically, the aperture stop S is positioned at an apex of an image-side surface of the planoconcave negative lens L4.

The third lens group G3 includes a planoconvex positive lens L6 of which an image side is a flat surface, a biconvex positive lens L7, and a planoconcave negative lens L8 of which an image side is a flat surface. Here, a cemented lens is formed by the biconvex positive lens L7 and the planoconcave negative lens L8.

A plane parallel plate F1 is disposed between the planoconcave negative lens L1 and the positive meniscus lens L2. The plane parallel plate F1 is an infrared cut filter. A plane parallel plate F2 and a plane parallel plate F3 are disposed on the image side of the third lens group G3. The plane parallel plate F2 is a cover glass. The plane parallel plate F3 is an imager glass.

With the switch-over from the normal observation to the magnified observation, the second lens group G2 moves toward the image side. In the movement of the second lens group G2, the planoconcave negative lens L4, the aperture stop S, and the negative meniscus lens L5 move integrally.

FIG. 4A, FIG. 4B, FIG. 4C, and FIG. 4D are aberration diagrams of a spherical aberration (SA), an astigmatism (AS), a distortion (DT), and a chromatic aberration of magnification (CC) respectively, in the normal observation state of the example 1. FIG. 4E, FIG. 4F, FIG. 4G, and FIG. 4H are aberration diagrams of a spherical aberration (SA), an astigmatism (AS), a distortion (DT), and a chromatic aberration of magnification (CC) respectively, in the magnified observation state of the example 1.

In each aberration diagram, a horizontal axis indicates an amount of aberration. The unit of the amount of aberration for the spherical aberration, the astigmatism, and the chromatic aberration of magnification is mm. Moreover, the unit of the amount of aberration for the distortion is % (percentage). Furthermore, ω is a half angle of view and the unit thereof is ° (degrees) and FNO denotes an F-number. Also, the unit of a wavelength of an aberration curve is nm. Same is the case for other examples.

EXAMPLE 2

Figure 5A:
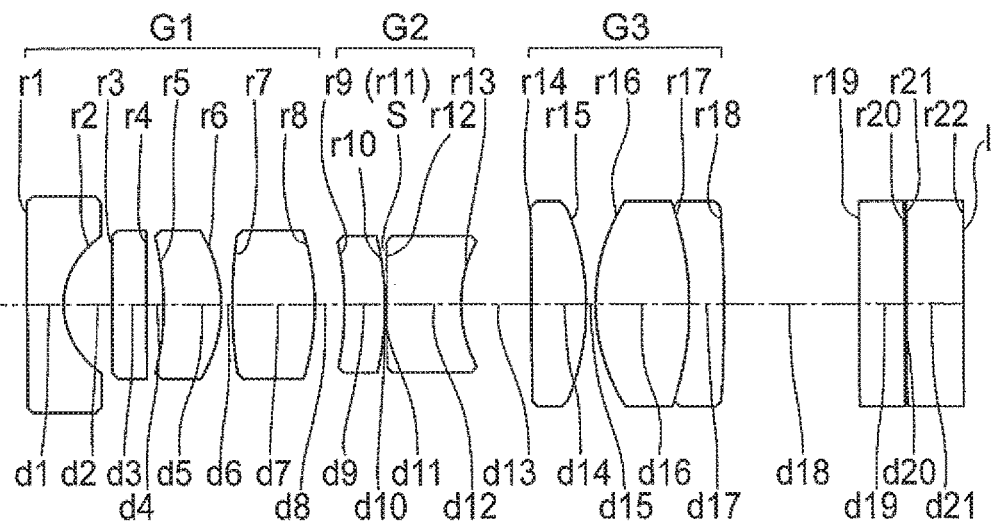
FIG. 5A and FIG. 5B are lens cross-sectional views of an endoscope objective optical system of an example 2.
Figure 5B:
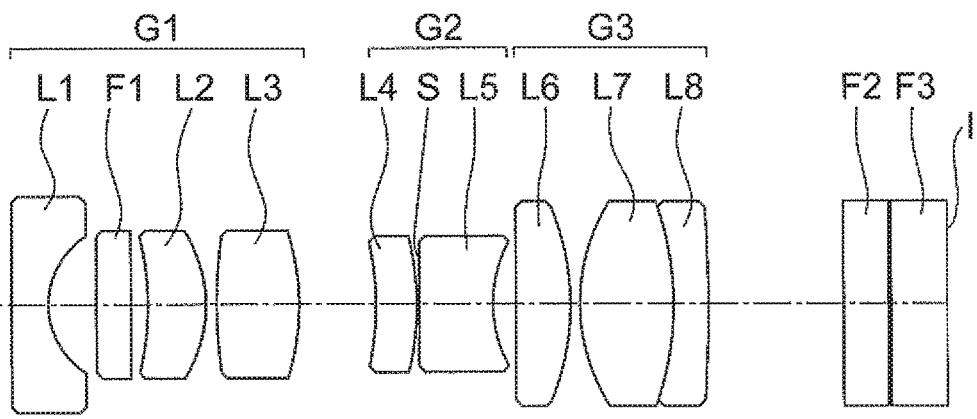

An endoscope objective optical system according to an example 2 will be described below. FIG. 5A and FIG. 5B are lens cross-sectional views of the endoscope objective optical system according to the example 2, where, FIG. 5A is a cross-sectional view in a normal observation state, and FIG. 5B is a cross-sectional view in a magnified observation state.

The endoscope objective optical system of the example 2 includes in order form an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3.

The second lens group G2 includes a positive meniscus lens L4 having a convex surface directed toward the image side and a planoconcave negative lens L5 of which an object side is a flat surface. The front group includes the positive meniscus lens L4 and the rear group includes the planoconcave negative lens L5.

An aperture stop S is disposed between the positive meniscus lens L4 and the planoconcave negative lens L5. More specifically, the aperture stop S is positioned at an apex of an object-side surface of the planoconcave negative lens L5.

The third lens group G3 includes a planoconvex positive lens L6 of which an object side is a flat surface, a biconvex positive lens L7, and a negative meniscus lens L8 having a convex surface directed toward the image side. Here, a cemented lens is formed by the biconvex positive lens L7 and the negative meniscus lens L8.

A plane parallel plate F1 is disposed between the planoconcave negative lens L1 and the positive meniscus lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the positive meniscus lens L4, the aperture stop S, and the planoconcave negative lens L5 move integrally.

FIG. 6A, FIG. 6B, FIG. 6C, and FIG. 6D are aberration diagrams of a spherical aberration (SA), an astigmatism (AS), a distortion (DT), and a chromatic aberration of magnification (CC) respectively, in the normal observation state of the example 2. FIG. 6E, FIG. 6F, FIG. 6G, and FIG. 6H are aberration diagrams of a spherical aberration (SA), an astigmatism (AS), a distortion (DT), and a chromatic aberration of magnification (CC) respectively, in the magnified observation state of the example 2.

EXAMPLE 3

Figure 7A:
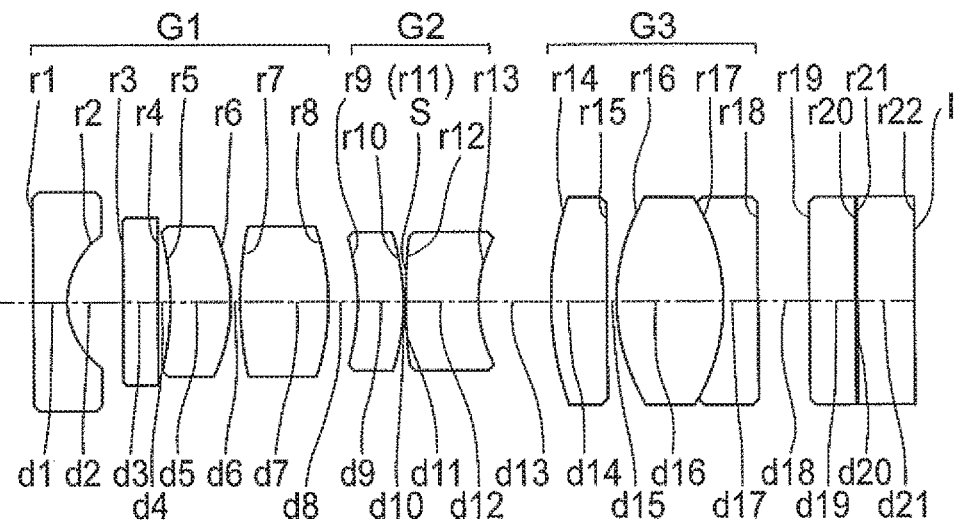
FIG. 7A and FIG. 7B are lens cross-sectional views of an endoscope objective optical system of an example 3.
Figure 7B:
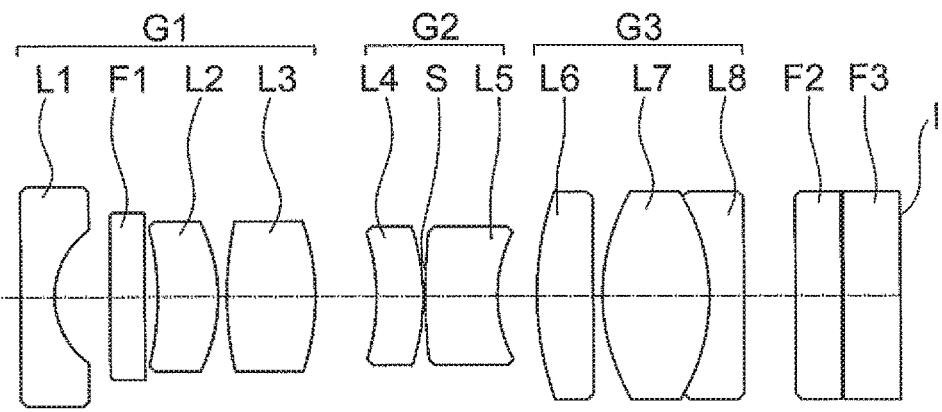

An endoscope objective optical system according to an example 3 will be described below. FIG. 7A and FIG. 7B are lens cross-sectional views of the endoscope objective optical system according to the example 3, where, FIG. 7A is a cross-sectional view in a normal observation state, and FIG. 7B is a cross-sectional view in a magnified observation state.

The endoscope objective optical system of the example 3 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3.

The second lens group G2 includes a positive meniscus lens L4 having a convex surface directed toward the image side and a negative meniscus lens L5 having a convex surface directed toward the object side. The front group includes the positive meniscus lens L4 and the rear group includes the negative meniscus lens L5.

An aperture stop S is disposed between the positive meniscus lens L4 and the negative meniscus lens L5. More specifically, the aperture stop S is positioned at an apex of an object-side surface of the negative meniscus lens L5.

The third lens group G3 includes a planoconvex positive lens L6 of which an image side is a flat surface, a biconvex positive lens L7, and a planoconcave negative lens L8 of which an image side is a flat surface. Here, a cemented lens is formed by the biconvex positive lens L7 and the planoconcave negative lens L8.

A plane parallel plate F1 is disposed between the planoconcave negative lens L1 and the positive meniscus lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the positive meniscus lens L4, the aperture stop S, and the negative meniscus lens L5 move integrally.

FIG. 8A, FIG. 8B, FIG. 8C, and FIG. 8D are aberration diagrams of a spherical aberration (SA), an astigmatism (AS), a distortion (DT), and a chromatic aberration of magnification (CC) respectively, in the normal observation state of the example 3. FIG. 8E, FIG. 8F, FIG. 8G, and FIG. 8H are aberration diagrams of a spherical aberration (SA), an astigmatism (AS), a distortion (DT), and a chromatic aberration of magnification (CC) respectively, in the magnified observation state of the example 3.

EXAMPLE 4

Figure 9A:
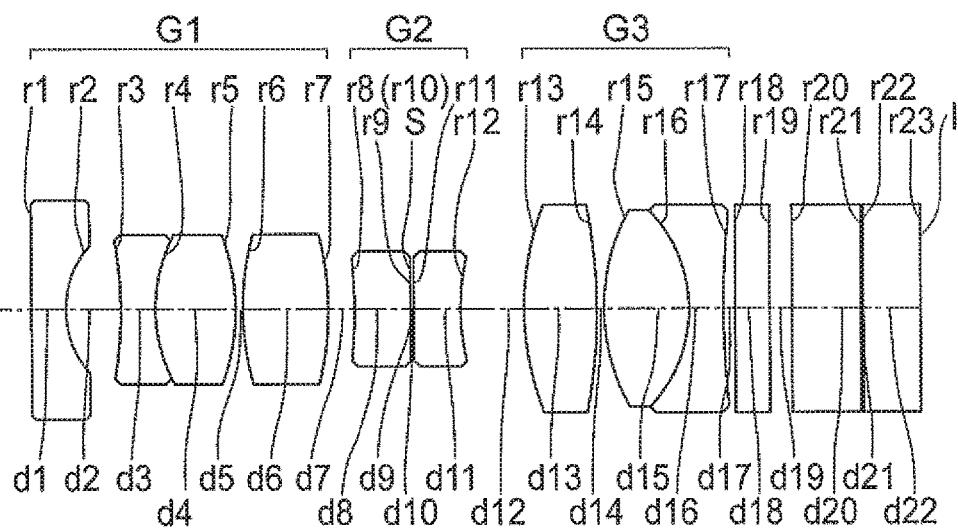
FIG. 9A and FIG. 9B are lens cross-sectional views of an endoscope objective optical system of an example 4.
Figure 9B:
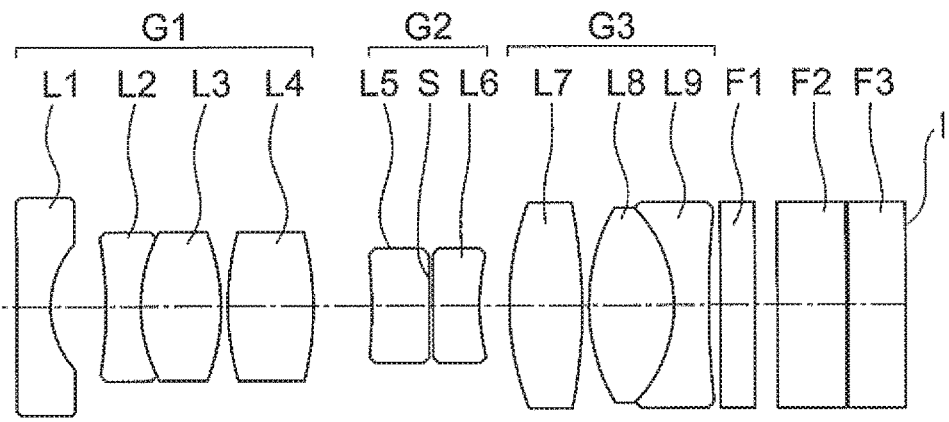

An endoscope objective optical system according to an example 4 will be described below. FIG. 9A and FIG. 9B are lens cross-sectional views of the endoscope objective optical system according to the example 4, where, FIG. 9A is a cross-sectional view in a normal observation state, and FIG. 9B is a cross-sectional view in a magnified observation state.

The endoscope objective optical system of the example 4 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a biconcave negative lens L2, a biconvex positive lens L3, and a biconvex positive lens L4. Here, a cemented lens is formed by the biconcave negative lens L2 and a biconvex positive lens L3.

The second lens group G2 includes a planoconcave negative lens L5 of which an image side is a flat surface and a planoconcave negative lens L6 of which an object side is a flat surface. The front group includes the planoconcave negative lens L5 and the rear group includes the planoconcave negative lens L6.

An aperture stop S is disposed between the planoconcave negative lens L5 and the planoconcave negative lens L6. More specifically, the aperture stop S is positioned at an apex of an image-side surface of the planoconcave negative lens L5.

The third lens group G3 includes a biconvex positive lens L7, a biconvex positive lens L8, and a biconcave negative lens L9. Here, a cemented lens is formed by the biconvex positive lens L8 and the biconcave negative lens L9.

A plane parallel plate F1, a plane parallel plate F2, and a plane parallel plate F3 are is disposed on the image side of the third lens group G3.

With the switch-over from the normal observation to the magnified observation, the second lens group G2 moves toward the image side. In the movement of the second lens group G2, the planoconcave negative lens L5, the aperture stop S, and the planoconcave negative lens L6 move integrally.

FIG. 10A, FIG. 10B, FIG. 10C, and FIG. 10D are aberration diagrams of a spherical aberration (SA), an astigmatism (AS), a distortion (DT), and a chromatic aberration of magnification (CC) respectively, in the normal observation state of the example 4. FIG. 10E, FIG. 10F, FIG. 10G, and FIG. 10H are aberration diagrams of a spherical aberration (SA), an astigmatism (AS), a distortion (DT), and a chromatic aberration of magnification (CC) respectively, in the magnified observation state of the example 4.

EXAMPLE 5

Figure 11A:
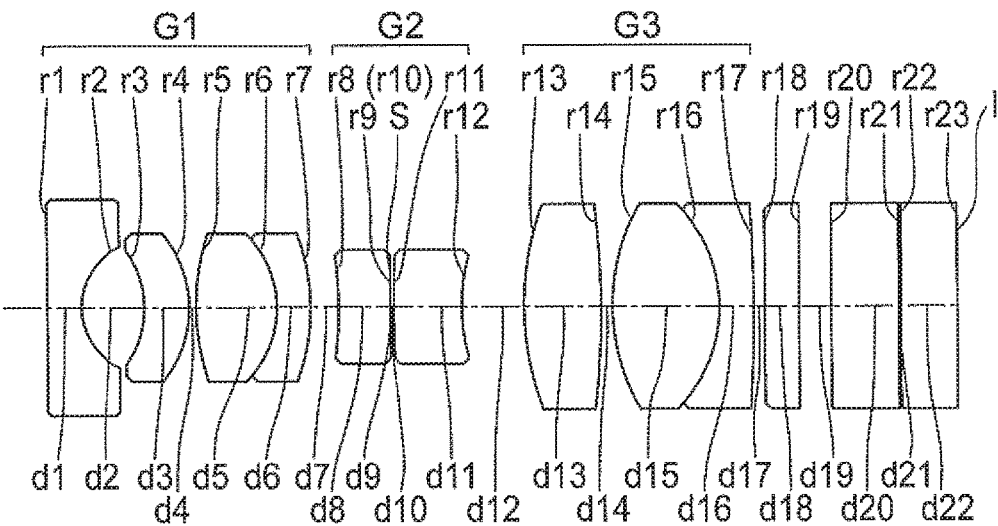
FIG. 11A and FIG. 11B are lens cross-sectional views of an endoscope objective optical system of an example 5.
Figure 11B:
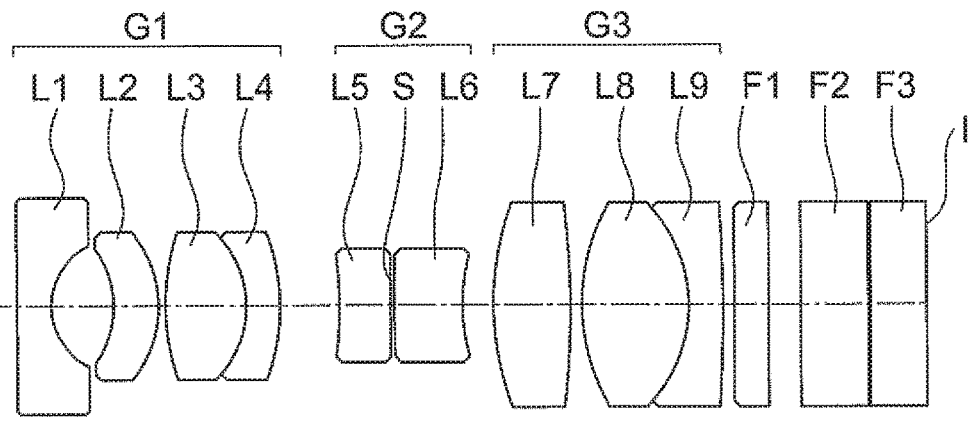

An endoscope objective optical system according to an example 5 will be described below. FIG. 11A and FIG. 11B are lens cross-sectional views of the endoscope objective optical system according to the example 5, where, FIG. 11A is a cross-sectional view in a normal observation state, and FIG. 11B is a cross-sectional view in a magnified observation state.

The endoscope objective optical system of the example 5 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a negative meniscus lens L2 having a convex surface directed toward an image side, a biconvex positive lens L3, and a negative meniscus lens L4 having a convex surface directed toward the image side. Here, a cemented lens is formed by the biconvex positive lens L3 and the negative meniscus lens L4.

The second lens group G2 includes a planoconcave negative lens L5 of which an image side is a flat surface and a negative meniscus lens L6 having a convex surface directed toward the object side. The front group includes the planoconcave negative lens L5 and the rear group includes the negative meniscus lens L6.

An aperture stop S is disposed between the planoconcave negative lens L5 and the negative meniscus lens L6. More specifically, the aperture stop S is positioned at an apex of an image-side surface of the planoconcave negative lens L5.

The third lens group G3 includes a biconvex positive lens L7, a biconvex positive lens L8, and a negative meniscus lens L9 having a convex surface directed toward the image side. Here, a cemented lens is formed by the biconvex positive lens L8 and the negative meniscus lens L9.

A plane parallel plate F1, a plane parallel plate F2, and a plane parallel plate F3 are disposed on the image side of the third lens group G3.

With the switch-over from the normal observation to the magnified observation, the second lens group G2 moves toward the image side. In the movement of the second lens group G2, the planoconcave negative lens L5, the aperture stop S, and the negative meniscus lens L6 move integrally.

FIG. 12A, FIG. 12B, FIG. 12C, and FIG. 12D are aberration diagrams of a spherical aberration (SA), an astigmatism (AS), a distortion (DT), and a chromatic aberration of magnification (CC) respectively, in the normal observation state of the example 5. FIG. 12E, FIG. 12F, FIG. 12G, and FIG. 12H are aberration diagrams of a spherical aberration (SA), an astigmatism (AS), a distortion (DT), and a chromatic aberration of magnification (CC) respectively, in the magnified observation state of the example 5.

EXAMPLE 6

Figure 13A:
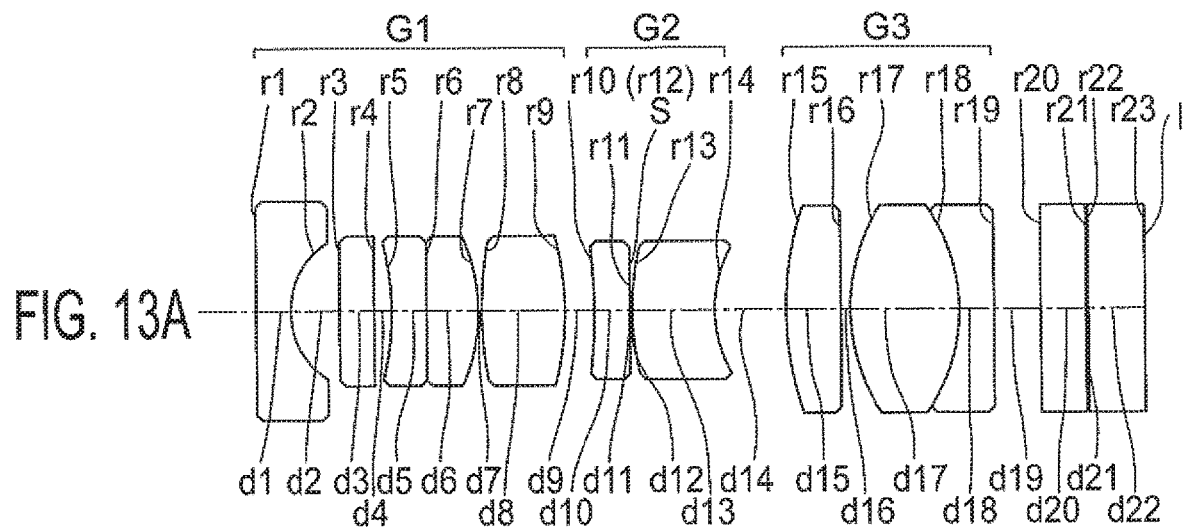
FIG. 13A and FIG. 13B are lens cross-sectional views of an endoscope objective optical system of an example 6.
Figure 13B:
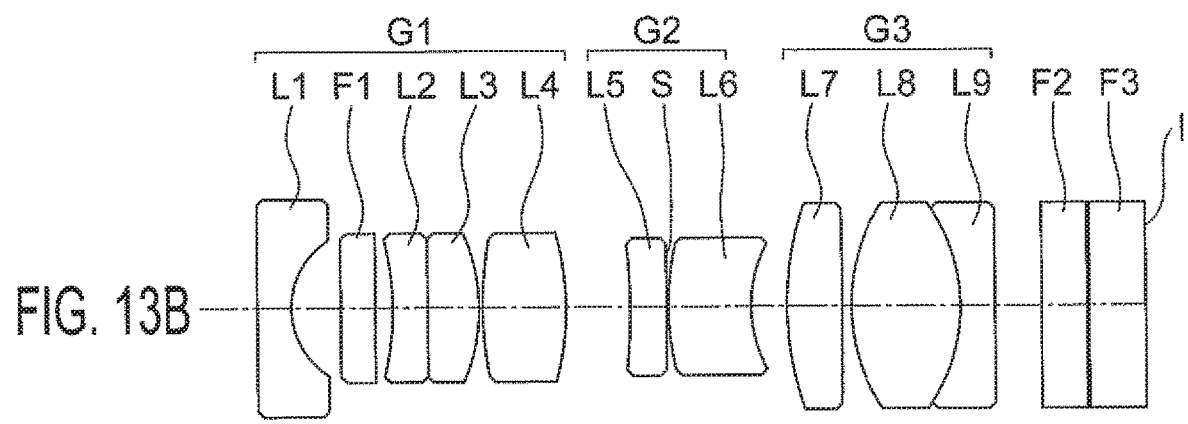

An endoscope objective optical system according to an example 6 will be described below. FIG. 13A and FIG. 13B are lens cross-sectional views of the endoscope objective optical system according to the example 6, where, FIG. 13A is a cross-sectional view in a normal observation state, and FIG. 13B is a cross-sectional view in a magnified observation state.

The endoscope objective optical system of the example 6 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a planoconcave negative lens L2 of which an image side is a flat surface, a planoconvex positive lens L3 of which an object side is a flat surface, and a biconvex positive lens L4. Here, a cemented lens is formed by the planoconcave negative lens L2 and the planoconvex positive lens L3.

The second lens group G2 includes a planoconcave negative lens L5 of which an image side is a flat surface and a negative meniscus lens L6 having a convex surface directed toward the object side. The front group includes the planoconcave negative lens L5 and the rear group includes the negative meniscus lens L6.

An aperture stop S is disposed between the planoconcave negative lens L5 and the negative meniscus lens L6. More specifically, the aperture stop S is positioned at an apex of an image-side surface of the planoconcave negative lens L5.

The third lens group G3 includes a biconvex positive lens L7, a biconvex positive lens L8, and a negative meniscus lens L9 having a convex surface directed toward the image side. Here, a cemented lens is formed by the biconvex positive lens L8 and the negative meniscus lens L9.

A plane parallel plate F1 is disposed between the planoconcave negative lens L1 and the planoconcave negative lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the planoconcave negative lens L5, the aperture stop S, and the negative meniscus lens L6 move integrally.

FIG. 14A, FIG. 14B, FIG. 14C, and FIG. 14D are aberration diagrams of a spherical aberration (SA), an astigmatism (AS), a distortion (DT), and a chromatic aberration of magnification (CC) respectively, in the normal observation state of the example 6. FIG. 14E, FIG. 14F, FIG. 14G, and FIG. 14H are aberration diagrams of a spherical aberration (SA), an astigmatism (AS), a distortion (DT), and a chromatic aberration of magnification (CC) respectively, in the magnified observation state of the example 6.

EXAMPLE 7

Figure 15A:
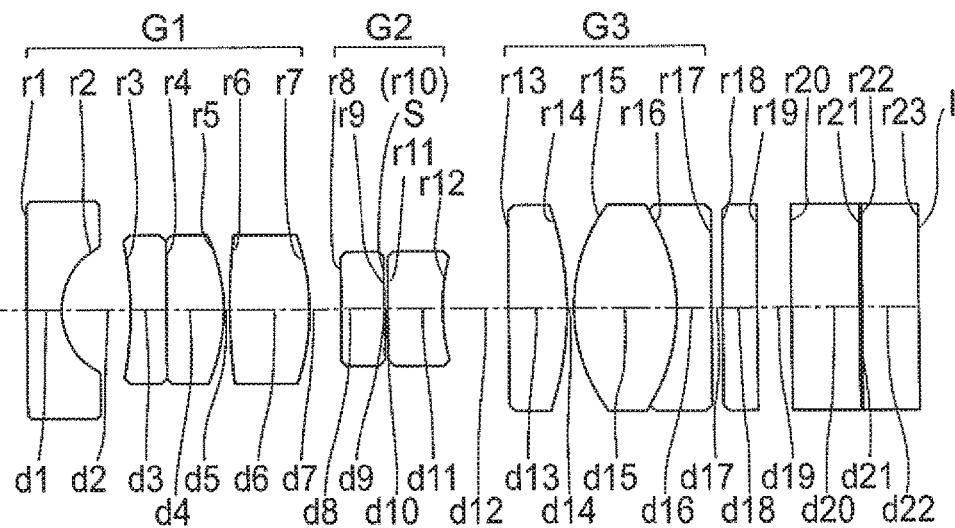
FIG. 15A and FIG. 15B are lens cross-sectional views of an endoscope objective optical system of an example 7.
Figure 15B:
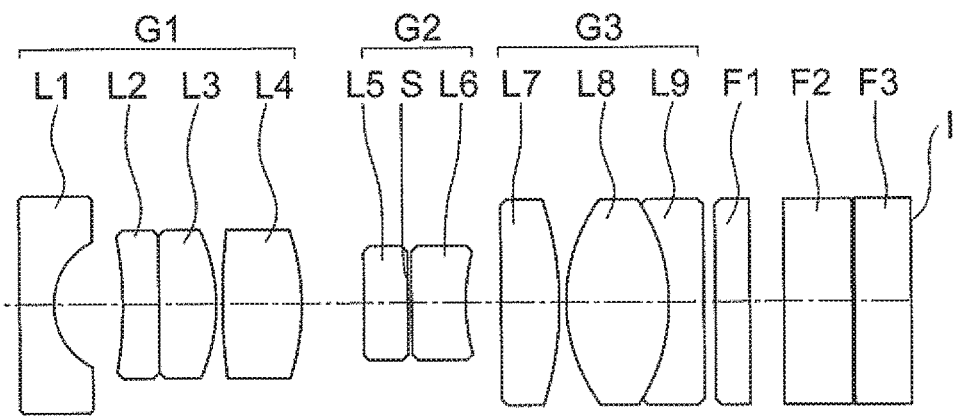

An endoscope objective optical system according to an example 7 will be described below. FIG. 15A and FIG. 15B are lens cross-sectional views of the endoscope objective optical system according to the example 7, where, FIG. 15A is a cross-sectional view in a normal observation state, and FIG. 15B is a cross-sectional view in a magnified observation state.

The endoscope objective optical system of the example 7 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a planoconcave negative lens L2 of which is an image side is a flat surface, a planoconvex positive lens L3 of which an object side is a flat surface, and a biconvex positive lens L4. Here, a cemented lens is formed by the planoconcave negative lens L2 and the planoconvex positive lens L3.

The second lens group G2 includes a planoconcave negative lens L5 of which an image side is a flat surface and a planoconcave negative lens L6 of which an object side is a flat surface. The front group includes the planoconcave negative lens L5 and the rear group includes the planoconcave negative lens L6.

An aperture stop S is disposed between the planoconcave negative lens L5 and the planoconcave negative lens L6.

More specifically, the aperture stop S is positioned at an apex of an image-side surface of the planoconcave negative lens L5.

The third lens group G3 includes a planoconvex positive lens L7 of which an object side is a flat surface, a biconvex positive lens L8, and a planoconcave negative lens L9 of which an image side is a flat surface. Here, a cemented lens is formed by the biconvex positive lens L8 and the planoconcave negative lens L9.

A plane parallel plate F1, a plane parallel plate F2, and a plane parallel plate F3 are disposed on the image side of the third lens group G3.

With the switch-over from the normal observation to the magnified observation, the second lens group G2 moves toward the image side. In the movement of the second lens group G2, the planoconcave negative lens L5, the aperture stop S, and the planoconcave negative lens L6 move integrally.

FIG. 16A, FIG. 16B, FIG. 16C, and FIG. 16D are aberration diagrams of a spherical aberration (SA), an astigmatism (AS), a distortion (DT), and a chromatic aberration of magnification (CC) respectively, in the normal observation state of the example 7. FIG. 16E, FIG. 16F, FIG. 16G, and FIG. 16H are aberration diagrams of a spherical aberration (SA), an astigmatism (AS), a distortion (DT), and a chromatic aberration of magnification (CC) respectively, in the magnified observation state of the example 7.

EXAMPLE 8

Figure 17A:
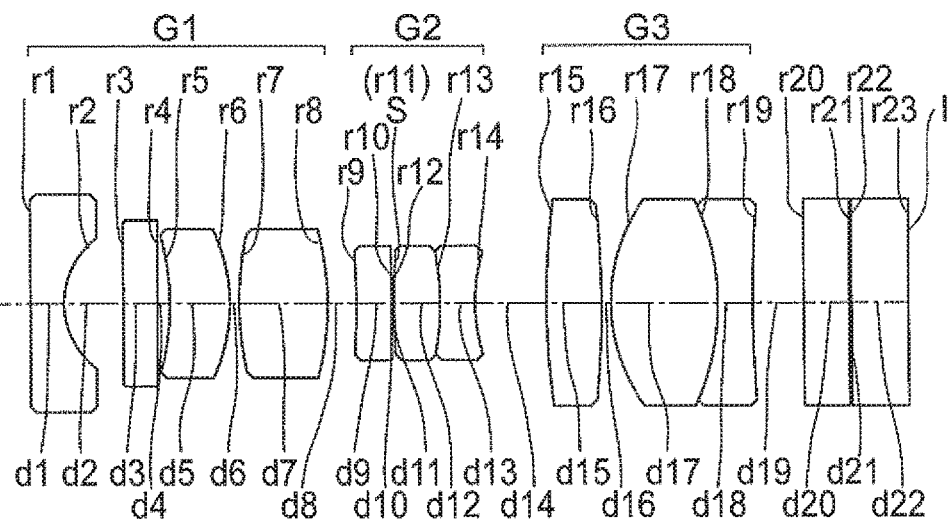
FIG. 17A and FIG. 17B are lens cross-sectional views of an endoscope objective optical system of an example 8.
Figure 17B:
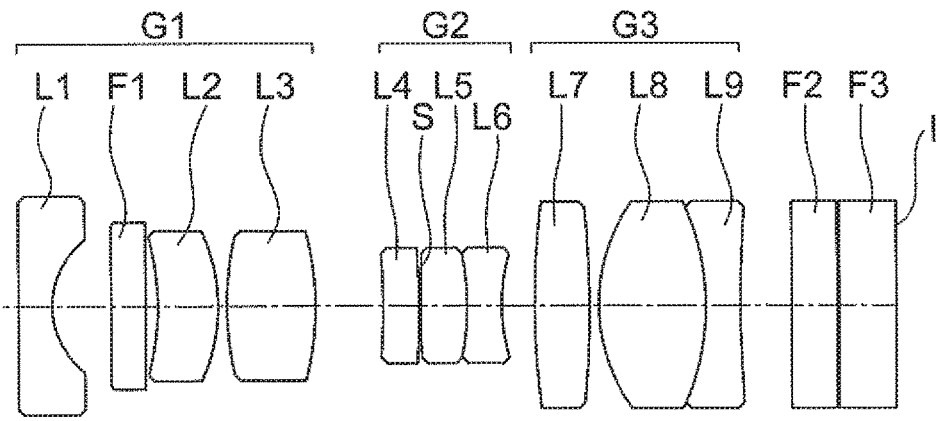

An endoscope objective optical system according to an example 8 will be described below. FIG. 17A and FIG. 17B are lens cross-sectional views of the endoscope objective optical system according to the example 8, where, FIG. 17A is a cross-sectional view in a normal observation state, and FIG. 17B is a cross-sectional view in a magnified observation state.

The endoscope objective optical system of the example 8 includes in order from an object side, a first lens group G1 having a positive refractive power, a second lens group G2 having a negative refractive power, and a third lens group G3 having a positive refractive power.

The first lens group G1 includes a planoconcave negative lens l1 of which an object side is a flat surface, a positive meniscus lens L2 having a convex surface directed toward an image side, and a biconvex positive lens L3.

The second lens group G2 includes a negative meniscus lens L4 having a convex surface directed toward the image side, a biconvex positive lens L5, and a biconcave negative lens L6. Here, a cemented lens is formed by the biconvex positive lens L5 and the biconcave negative lens L6. The front group includes the negative meniscus lens L4 and the rear group includes the biconvex positive lens L5 and the biconcave negative lens L6.

An aperture stop S is disposed between the negative meniscus lens L4 and the biconvex positive lens L5. More specifically, the aperture stop S is positioned at an apex of an object-side surface of the biconvex positive lens L5.

The third lens group G3 includes a biconvex positive lens L7, a biconvex positive lens L8, and a biconcave negative lens L9. Here, a cemented lens is formed by the biconvex positive lens L8 and the biconcave negative lens L9.

A plane parallel plate F1 is disposed between the planoconcave negative lens L1 and the positive meniscus lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the negative meniscus lens L4, the aperture stop S, the biconvex positive lens L5, and the biconcave negative lens L6 move integrally.

FIG. 18A, FIG. 18B, FIG. 18C, and FIG. 18D are aberration diagrams of a spherical aberration (SA), an astigmatism (AS), a distortion (DT), and a chromatic aberration of magnification (CC) respectively, in the normal observation state of the example 8. FIG. 18E, FIG. 18F, FIG. 18G, and FIG. 18H are aberration diagrams of a spherical aberration (SA), an astigmatism (AS), distortion (DT), and a chromatic aberration of magnification (CC) respectively, in the magnified observation state of the example 8.

EXAMPLE 9

Figure 19A:
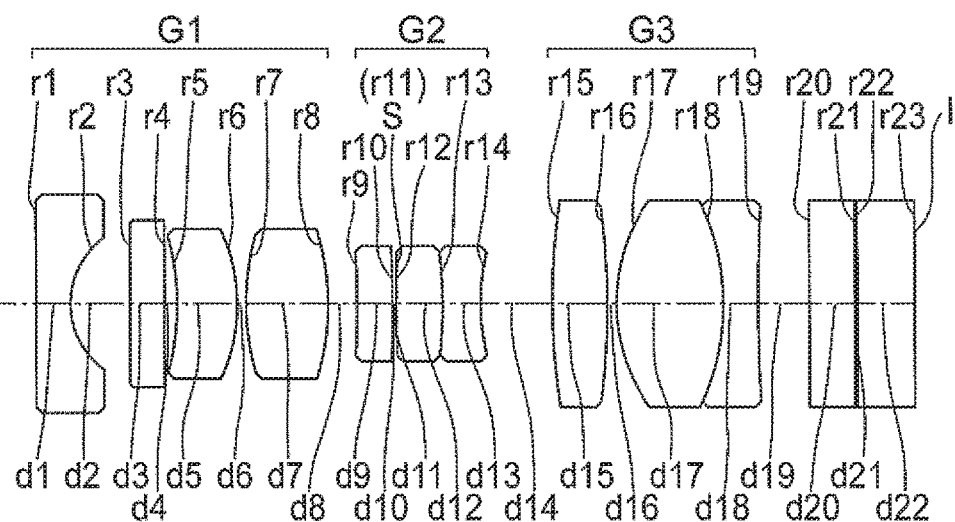
FIG. 19A and FIG. 19B are lens cross-sectional views of an endoscope objective optical system of an example 9.
Figure 19B:
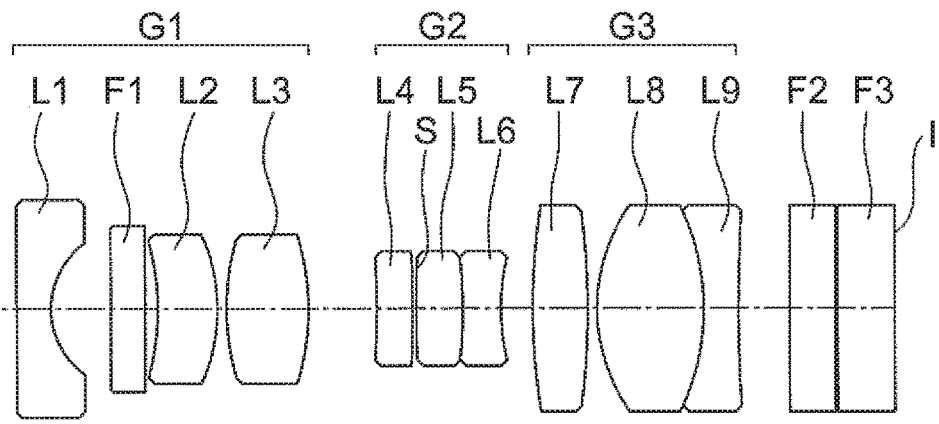

An endoscope objective optical system according to an example 9 will be described below. FIG. 19A and FIG. 19B are lens cross-sectional views of the endoscope objective optical system according to the example 9, where, FIG. 19A is a cross-sectional view in a normal observation state, and FIG. 19B is a cross-sectional view in a magnified observation state.

The endoscope objective optical system of the example 9 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3.

The second lens group G2 includes a negative meniscus lens L4 having a convex surface directed toward the image side, a biconvex positive lens L5, and a biconcave negative lens L6. Here, a cemented lens is formed by the biconvex positive lens L5 and the biconcave negative lens L6. The front group includes the negative meniscus lens L4 and the rear group includes the biconvex positive lens L5 and the biconcave negative lens L5.

An aperture stop S is disposed between the negative meniscus lens L4 and the biconvex positive lens L5. More specifically, the aperture stop S is positioned at an apex of an object-side surface of the biconvex positive lens L5.

The third lens group G3 includes a biconvex positive lens L7, a biconvex positive lens L8, and a biconcave negative lens L9. Here, a cemented lens is formed by the biconvex positive lens L8 and the biconcave negative lens L9.

A plane parallel plate F1 is disposed between the planoconcave negative lens L1 and the positive meniscus lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the negative meniscus lens L4, the aperture stop S, the biconvex positive lens L5, and the biconcave negative lens L6 move integrally.

FIG. 20A, FIG. 20B, FIG. 20C, and FIG. 20D are aberration diagrams of a spherical aberration (SA), an astigmatism (AS), a distortion (DT), and a chromatic aberration of magnification (CC) respectively, in the normal observation state of the example 9. FIG. 20E, FIG. 20F, FIG. 20G, and FIG. 20H are aberration diagrams of a spherical aberration (SA), an astigmatism (AS), a distortion (DT), and a chromatic aberration of magnification (CC) respectively, in the magnified observation state of the example 9.

EXAMPLE 10

Figure 21A:
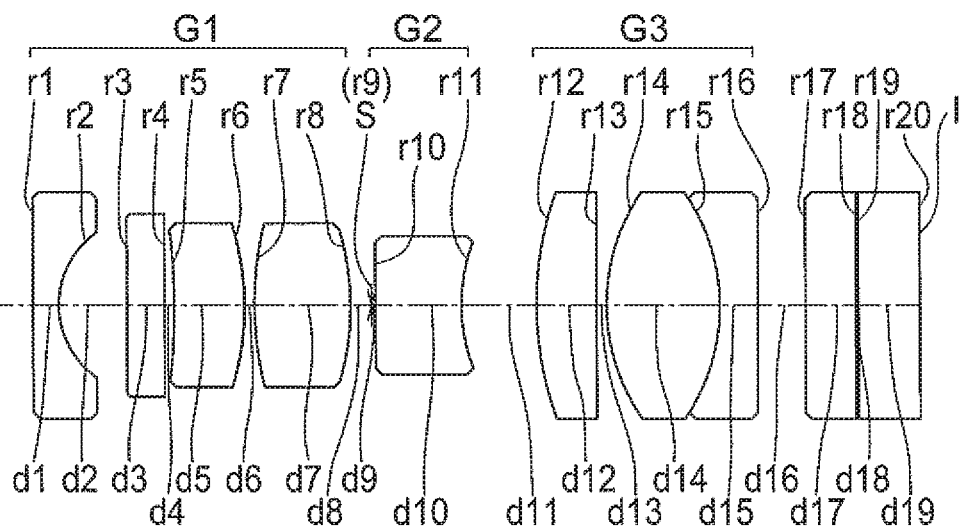
FIG. 21A and FIG. 21B are lens cross-sectional views of an endoscope objective optical system of an example 10.
Figure 21B:
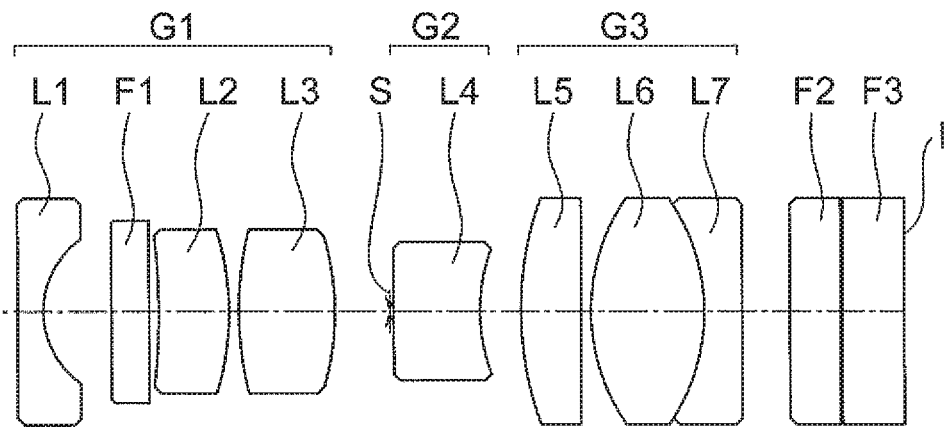

An endoscope objective optical system according to an example 10 will be described below. FIG. 21A and FIG. 21B are lens cross-sectional views of the endoscope objective optical system according to the example 10, where, FIG. 21A is a cross-sectional view in a normal observation state, and FIG. 21B is a cross-sectional view in a magnified observation state.

The endoscope objective optical system of the example 10 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3.

The second lens group G2 includes a planoconcave negative lens L4 of which an object side is a flat surface.

An aperture stop S is disposed near an object-side surface of the planoconcave negative lens L4.

The third lens group G3 includes a planoconvex positive lens L5 of which an image side is a flat surface, a biconvex positive lens L6, and a planoconcave negative lens L7 of which an image side is a flat surface. Here, a cemented lens is formed by the biconvex positive lens L6 and the planoconcave negative lens L7.

A plane parallel plate F1 is disposed between the planoconcave negative lens L1 and the positive meniscus lens L2. A plane parallel plate F2 and a plane parallel plate F3 are disposed on the image side of the third lens group G3.

With the switch-over from the normal observation to the magnified observation, the second lens group G2 moves toward the image side. In the movement of the second lens group G2, the aperture stop S and the planoconcave negative lens L4 move integrally.

FIG. 22A, FIG. 22B, FIG. 22C, and FIG. 22D are aberration diagrams of a spherical aberration (SA), an astigmatism (AS), a distortion (DT), and a chromatic aberration of magnification (CC) respectively, in the normal observation state of the example 10. FIG. 22E, FIG. 22F, FIG. 22G, and FIG. 22H are aberration diagrams of a spherical aberration (SA), an astigmatism (AS), a distortion (DT), and a chromatic aberration of magnification (CC) respectively, in the magnified observation state of the example 10.

Numerical data of each example described above is shown below. In Surface data, r denotes radius of curvature of each lens surface, d denotes a distance between respective lens surfaces, ne denotes a refractive index of each lens for a e-line, vd denotes an Abbe number for each lens and stop denotes an aperture stop.

In Various data, OBJ denotes an object distance, f denotes a focal length at e-line, FNO. denotes an F number, ω denotes a half angle of view, IH denotes an image height.

EXAMPLE 1

Unit mm

Surface data

| Surface no. | r | d | ne | vd |
|---|---|---|---|---|
| 1 | ∞ | 0.300 | 1.77066 | 71.8 |
| 2 | 0.7030 | 0.480 | | |
| 3 | ∞ | 0.300 | 1.52300 | 65.1 |
| 4 | ∞ | 0.110 | | |
| 5 | −2.4610 | 0.520 | 1.51825 | 63.9 |
| 6 | −1.4850 | 0.080 | | |
| 7 | 2.9200 | 0.770 | 1.75844 | 52.1 |
| 8 | −1.9610 | Variable | | |
| 9 | −2.8190 | 0.310 | 1.85504 | 23.6 |

-continued

Unit mm

| | | | | |
|---|---|---|---|---|
| 10 | ∞ | 0.000 | | |
| 11 (Stop) | ∞ | 0.020 | | |
| 12 | 2.7030 | 0.720 | 1.97189 | 17.3 |
| 13 | 1.4440 | Variable | | |
| 14 | 2.7030 | 0.480 | 1.88815 | 40.5 |
| 15 | ∞ | 0.080 | | |
| 16 | 1.7170 | 0.930 | 1.73234 | 54.5 |
| 17 | −1.7170 | 0.300 | 2.01169 | 28.1 |
| 18 | ∞ | 0.450 | | |
| 19 | ∞ | 0.400 | 1.51825 | 64.1 |
| 20 | ∞ | 0.020 | 1.51500 | 64.0 |
| 21 | ∞ | 0.500 | 1.61350 | 50.5 |
| 22 (Image plane) | ∞ | | | |

Various data

| | Normal observation | magnified observation |
|---|---|---|
| OBJ | 12.00 | 2.85 |
| f | 0.99 | 1.07 |
| Fno | 5.63 | 5.85 |
| ω (°) | 106.8° | 80.5° |
| IH (mm) | 0.75 | 0.75 |
| d8 | 0.260 | 0.540 |
| d13 | 0.620 | 0.340 |

EXAMPLE 2

Unit mm

Surface data

| Surface no. | r | d | ne | vd |
|---|---|---|---|---|
| 1 | ∞ | 0.320 | 1.88815 | 40.8 |
| 2 | 0.7063 | 0.430 | | |
| 3 | ∞ | 0.300 | 1.52300 | 65.1 |
| 4 | ∞ | 0.150 | | |
| 5 | −2.4918 | 0.510 | 1.69979 | 55.3 |
| 6 | −1.2267 | 0.090 | | |
| 7 | 4.2141 | 0.730 | 1.73234 | 54.5 |
| 8 | −2.0953 | Variable | | |
| 9 | −2.6363 | 0.357 | 2.01169 | 28.1 |
| 10 | −2.5243 | 0.020 | | |
| 11 (Stop) | ∞ | 0.000 | | |
| 12 | ∞ | 0.643 | 2.01169 | 28.3 |
| 13 | 1.1524 | Variable | | |
| 14 | ∞ | 0.480 | 1.88815 | 40.8 |
| 15 | −2.2296 | 0.080 | | |
| 16 | 1.7072 | 0.823 | 1.59143 | 60.9 |
| 17 | −2.6473 | 0.300 | 1.97189 | 17.3 |
| 18 | −12.0134 | 1.188 | | |
| 19 | ∞ | 0.400 | 1.51825 | 64.1 |
| 20 | ∞ | 0.020 | 1.51500 | 64.0 |
| 21 | ∞ | 0.500 | 1.61350 | 50.5 |
| 22 (Image plane) | ∞ | | | |

Various data

| | Normal observation | magnified observation |
|---|---|---|
| OBJ | 12.00 | 3.50 |
| f | 0.95 | 1.26 |
| Fno | 5.31 | 6.26 |
| ω (°) | 104.3° | 62.2° |
| IH (mm) | 0.75 | 0.75 |
| d8 | 0.260 | 0.680 |
| d13 | 0.620 | 0.200 |

EXAMPLE 3

Unit mm

Surface data

| Surface no. | r | d | ne | vd |
|---|---|---|---|---|
| 1 | ∞ | 0.300 | 1.77066 | 71.8 |
| 2 | 0.7030 | 0.480 | | |
| 3 | ∞ | 0.300 | 1.52300 | 65.1 |
| 4 | ∞ | 0.110 | | |
| 5 | −2.4610 | 0.520 | 1.51825 | 63.9 |
| 6 | −1.4850 | 0.080 | | |
| 7 | 2.9200 | 0.770 | 1.75844 | 52.1 |
| 8 | −1.9610 | Variable | | |
| 9 | −1.8000 | 0.402 | 1.85504 | 23.6 |
| 10 | −1.9191 | 0.020 | | |
| 11 (Stop) | ∞ | 0.000 | | |
| 12 | 5.0000 | 0.628 | 1.97189 | 17.3 |
| 13 | 1.1897 | Variable | | |
| 14 | 2.7030 | 0.480 | 1.88815 | 40.5 |
| 15 | ∞ | 0.080 | | |
| 16 | 1.7170 | 0.930 | 1.73234 | 54.5 |
| 17 | −1.7170 | 0.300 | 2.01169 | 28.1 |
| 18 | ∞ | 0.450 | | |
| 19 | ∞ | 0.400 | 1.51825 | 64.1 |
| 20 | ∞ | 0.020 | 1.51500 | 64.0 |
| 21 | ∞ | 0.500 | 1.61350 | 50.5 |
| 22 (Image plane) | ∞ | | | |

Various data

| | Normal observation | magnified observation |
|---|---|---|
| OBJ | 12.00 | 2.85 |
| f | 0.98 | 1.06 |
| Fno | 5.74 | 5.97 |
| ω (°) | 108.3° | 81.0° |
| IH (mm) | 0.75 | 0.75 |
| d8 | 0.260 | 0.540 |
| d13 | 0.630 | 0.340 |

EXAMPLE 4

Unit mm

Surface data

| Surface no. | r | d | ne | vd |
|---|---|---|---|---|
| 1 | ∞ | 0.300 | 1.77066 | 71.8 |
| 2 | 0.8299 | 0.473 | | |
| 3 | −3.5356 | 0.300 | 2.01169 | 28.1 |
| 4 | 1.3737 | 0.700 | 1.75844 | 52.1 |
| 5 | −1.8531 | 0.060 | | |
| 6 | 2.3120 | 0.750 | 1.88815 | 40.5 |
| 7 | −2.6375 | Variable | | |
| 8 | −4.9521 | 0.498 | 2.01169 | 28.1 |
| 9 | ∞ | 0.000 | | |
| 10 (Stop) | ∞ | 0.030 | | |
| 11 | ∞ | 0.400 | 2.01169 | 28.3 |
| 12 | 1.8571 | Variable | | |
| 13 | 2.4588 | 0.633 | 1.88815 | 40.5 |
| 14 | −4.6447 | 0.060 | | |
| 15 | 1.7303 | 0.745 | 1.69979 | 55.3 |
| 16 | −1.2308 | 0.300 | 2.01169 | 28.1 |
| 17 | 8.1714 | 0.100 | | |
| 18 | ∞ | 0.300 | 1.52300 | 65.1 |
| 19 | ∞ | 0.197 | | |
| 20 | ∞ | 0.600 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | | | |

Various data

| | Normal observation | magnified observation |
|---|---|---|
| OBJ | 11.50 | 3.25 |
| f | 1.03 | 1.16 |
| Fno | 5.39 | 5.82 |
| ω (°) | 90.8° | 66.3° |
| IH (mm) | 0.75 | 0.75 |
| d7 | 0.230 | 0.520 |
| d12 | 0.547 | 0.257 |

EXAMPLE 5

Unit mm

Surface data

| Surface no. | r | d | ne | vd |
|---|---|---|---|---|
| 1 | ∞ | 0.300 | 1.77066 | 71.8 |
| 2 | 0.5874 | 0.552 | | |
| 3 | −0.8605 | 0.393 | 2.01169 | 28.1 |
| 4 | −1.0217 | 0.060 | | |
| 5 | 2.0638 | 0.700 | 1.82017 | 46.4 |
| 6 | −0.9200 | 0.300 | 1.85504 | 23.6 |
| 7 | −1.8345 | Variable | | |
| 8 | −3.3916 | 0.459 | 1.88815 | 40.5 |
| 9 | ∞ | 0.000 | | |
| 10 (Stop) | ∞ | 0.030 | | |
| 11 | 13.6515 | 0.599 | 2.01169 | 28.1 |
| 12 | 1.6354 | Variable | | |
| 13 | 2.5409 | 0.675 | 1.88815 | 40.5 |
| 14 | −7.4142 | 0.100 | | |
| 15 | 1.8079 | 0.930 | 1.69979 | 55.3 |
| 16 | −1.2860 | 0.300 | 2.01169 | 28.1 |
| 17 | −13.7738 | 0.100 | | |
| 18 | ∞ | 0.300 | 1.52300 | 65.1 |
| 19 | ∞ | 0.283 | | |
| 20 | ∞ | 0.600 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | | | |

Various data

| | Normal observation | magnified observation |
|---|---|---|
| OBJ | 11.50 | 3.25 |
| f | 0.98 | 1.14 |
| Fno | 5.33 | 5.82 |
| ω (°) | 107.3° | 73.8° |
| IH (mm) | 0.75 | 0.75 |
| d7 | 0.250 | 0.527 |
| d12 | 0.549 | 0.272 |

EXAMPLE 6

Unit mm

Surface data

| Surface no. | r | d | ne | vd |
|---|---|---|---|---|
| 1 | ∞ | 0.300 | 1.77066 | 71.8 |
| 2 | 0.7030 | 0.430 | | |
| 3 | ∞ | 0.300 | 1.52300 | 65.1 |
| 4 | ∞ | 0.152 | | |
| 5 | −2.4390 | 0.300 | 2.01169 | 28.1 |
| 6 | ∞ | 0.450 | 1.73234 | 54.7 |
| 7 | −1.5821 | 0.030 | | |
| 8 | 3.1750 | 0.730 | 1.82017 | 46.4 |
| 9 | −2.4256 | Variable | | |
| 10 | −4.6121 | 0.310 | 2.01169 | 28.1 |
| 11 | ∞ | 0.000 | | |
| 12 (Stop) | ∞ | 0.020 | | |
| 13 | 2.4154 | 0.720 | 1.93430 | 18.7 |
| 14 | 1.1456 | Variable | | |
| 15 | 2.7365 | 0.480 | 1.88815 | 40.5 |
| 16 | −77.2763 | 0.080 | | |
| 17 | 1.6566 | 0.940 | 1.73234 | 54.5 |
| 18 | −1.5656 | 0.300 | 2.01169 | 28.1 |
| 19 | −1469.9702 | 0.410 | | |
| 20 | ∞ | 0.400 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | | | |

Various data

| | Normal observation | magnified observation |
|---|---|---|
| OBJ | 12.00 | 2.85 |
| f | 0.95 | 1.03 |
| Fno | 5.51 | 5.75 |
| ω (°) | 111.7° | 82.35° |
| IH (mm) | 0.75 | 0.75 |
| d9 | 0.260 | 0.565 |
| d14 | 0.620 | 0.315 |

EXAMPLE 7

Unit mm

Surface data

| Surface no. | r | d | ne | vd |
|---|---|---|---|---|
| 1 | ∞ | 0.300 | 1.77066 | 71.8 |
| 2 | 0.6146 | 0.602 | | |
| 3 | −3.3604 | 0.313 | 1.93430 | 18.7 |
| 4 | ∞ | 0.500 | 1.80811 | 46.6 |
| 5 | −1.5548 | 0.050 | | |
| 6 | 5.7019 | 0.700 | 1.82017 | 46.4 |
| 7 | −2.0235 | Variable | | |
| 8 | −19.7784 | 0.385 | 2.01169 | 28.1 |
| 9 | ∞ | 0.000 | | |
| 10 (Stop) | ∞ | 0.030 | | |
| 11 | ∞ | 0.473 | 2.01169 | 28.3 |
| 12 | 1.7147 | Variable | | |
| 13 | ∞ | 0.500 | 1.73234 | 54.7 |
| 14 | −2.9114 | 0.060 | | |
| 15 | 1.5213 | 0.900 | 1.73234 | 54.5 |
| 16 | −1.6229 | 0.300 | 2.01169 | 28.1 |
| 17 | ∞ | 0.100 | | |
| 18 | ∞ | 0.300 | 1.52300 | 65.1 |
| 19 | ∞ | 0.300 | | |
| 20 | ∞ | 0.600 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | | | |

Various data

| | Normal observation | magnified observation |
|---|---|---|
| OBJ | 11.50 | 2.90 |
| f | 0.96 | 1.05 |
| Fno | 5.64 | 5.9 |
| ω (°) | 109.5° | 83.1° |
| IH (mm) | 0.75 | 0.75 |
| d7 | 0.280 | 0.551 |
| d12 | 0.581 | 0.310 |

EXAMPLE 8

Unit mm

Surface data

| Surface no. | r | d | ne | vd |
|---|---|---|---|---|
| 1 | ∞ | 0.300 | 1.77066 | 71.8 |
| 2 | 0.7265 | 0.510 | | |
| 3 | ∞ | 0.300 | 1.52300 | 65.1 |
| 4 | ∞ | 0.110 | | |
| 5 | −2.1754 | 0.520 | 1.51825 | 63.9 |
| 6 | −1.5852 | 0.080 | | |
| 7 | 2.6313 | 0.770 | 1.82017 | 46.4 |
| 8 | −2.4479 | Variable | | |
| 9 | −6.3004 | 0.310 | 2.01169 | 28.1 |
| 10 | −11.9369 | 0.020 | | |
| 11 (Stop) | ∞ | 0.000 | | |
| 12 | 14.9442 | 0.400 | 2.01169 | 28.1 |
| 13 | −2.3569 | 0.300 | 1.85504 | 23.6 |
| 14 | 1.5468 | Variable | | |
| 15 | 6.7294 | 0.480 | 1.88815 | 40.5 |
| 16 | −8.4050 | 0.080 | | |
| 17 | 1.5307 | 0.930 | 1.73234 | 54.5 |
| 18 | −2.1409 | 0.300 | 2.01169 | 28.1 |
| 19 | 11.0751 | 0.450 | | |
| 20 | ∞ | 0.400 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | 0.000 | | |

Various data

| | Normal observation | magnified observation |
|---|---|---|
| OBJ | 12.00 | 2.85 |
| f | 1.01 | 1.07 |
| Fno | 5.66 | 5.74 |
| ω (°) | 103.1° | 79.4° |
| IH (mm) | 0.75 | 0.75 |
| d8 | 0.260 | 0.600 |
| d14 | 0.620 | 0.284 |

EXAMPLE 9

Unit mm

Surface data

| Surface no. | r | d | ne | vd |
|---|---|---|---|---|
| 1 | ∞ | 0.300 | 1.77066 | 71.8 |
| 2 | 0.7129 | 0.518 | | |
| 3 | ∞ | 0.300 | 1.52300 | 65.1 |
| 4 | ∞ | 0.110 | | |
| 5 | −2.2813 | 0.520 | 1.51825 | 63.9 |
| 6 | −1.5684 | 0.080 | | |
| 7 | 2.1863 | 0.719 | 1.69979 | 55.3 |
| 8 | −2.1826 | Variable | | |
| 9 | −7.1754 | 0.310 | 1.88815 | 40.5 |
| 10 | −9.7269 | 0.030 | | |
| 11 (Stop) | ∞ | 0.000 | | |
| 12 | 11.6454 | 0.400 | 1.77621 | 49.4 |
| 13 | −4.0836 | 0.325 | 2.01169 | 28.1 |
| 14 | 1.8826 | Variable | | |
| 15 | 5.7087 | 0.480 | 1.88815 | 40.5 |
| 16 | −6.6163 | 0.080 | | |
| 17 | 1.5481 | 0.930 | 1.73234 | 54.5 |
| 18 | −2.0839 | 0.300 | 2.01169 | 28.1 |
| 19 | 13.7216 | 0.450 | | |
| 20 | ∞ | 0.400 | 1.51825 | 64.1 |
| 21 | ∞ | 0.020 | 1.51500 | 64.0 |
| 22 | ∞ | 0.500 | 1.61350 | 50.5 |
| 23 (Image plane) | ∞ | 0.000 | | |

Various data

| | Normal observation | magnified observation |
|---|---|---|
| OBJ | 12.00 | 2.85 |
| f | 0.99 | 1.08 |
| Fno | 5.48 | 5.67 |
| ω (°) | 110.5° | 80.4° |
| IH (mm) | 0.75 | 0.75 |
| d8 | 0.260 | 0.602 |
| d14 | 0.620 | 0.278 |

EXAMPLE 10

Unit mm

Surface data

| Surface no. | r | d | ne | vd |
|---|---|---|---|---|
| 1 | ∞ | 0.200 | 1.77066 | 71.8 |
| 2 | 0.7030 | 0.540 | | |
| 3 | ∞ | 0.300 | 1.52300 | 65.1 |
| 4 | ∞ | 0.080 | | |
| 5 | −4.9950 | 0.560 | 1.75844 | 52.3 |
| 6 | −2.2560 | 0.080 | | |
| 7 | 2.5930 | 0.770 | 1.75844 | 52.3 |
| 8 | −2.1070 | Variable | | |
| 9 (Stop) | ∞ | 0.030 | | |
| 10 | ∞ | 0.680 | 1.85504 | 23.8 |
| 11 | 1.3810 | Variable | | |
| 12 | 2.5930 | 0.480 | 1.88815 | 40.8 |
| 13 | ∞ | 0.080 | | |
| 14 | 1.5810 | 0.900 | 1.69979 | 55.5 |
| 15 | −1.5810 | 0.300 | 2.01169 | 28.3 |
| 16 | ∞ | 0.380 | | |
| 17 | ∞ | 0.400 | 1.51825 | 64.1 |
| 18 | ∞ | 0.020 | 1.51500 | 64.0 |
| 19 | ∞ | 0.500 | 1.61350 | 50.5 |
| 20 (Image plane) | ∞ | 0.000 | | |

Unit mm

Various data

| | Normal observation | magnified observation |
|---|---|---|
| OBJ | 12.50 | 2.85 |
| f | 0.96 | 1.03 |
| Fno | 5.65 | 5.87 |
| ω (°) | 112.3° | 86.0° |
| IH (mm) | 0.754 | 0.754 |
| d8 | 0.170 | 0.440 |
| d11 | 0.600 | 0.330 |

The values of conditional expressions (1) to (6) in the first example to the tenth Example are shown below. '-' (hyphen) indicates that there is no corresponding arrangement.

| Conditional expression | Example 1 | Example 2 | Example 3 |
|---|---|---|---|
| (1) f2/fW | −1.64 | −1.19 | −1.67 |
| (2) f2F/f2 | 2.03 | −19.84 | −37.37 |
| (3) Σd2/D2 | 0.54 | 0.54 | 0.54 |
| (4) N2 | 1.85 | 2 | 1.85 |
| (5) P2/fW | −0.32 | −0.45 | −0.34 |
| (6) ΣL2F/ΣL2R | 0.46 | 0.56 | 0.68 |

| Conditional expression | Example 4 | Example 5 | Example 6 |
|---|---|---|---|
| (1) f2/fW | −1.21 | −1.17 | −1.73 |
| (2) f2F/f2 | 3.93 | 3.36 | 2.78 |
| (3) Σd2/D2 | 0.54 | 0.58 | 0.54 |
| (4) N2 | 2 | 1.88 | 2 |
| (5) P2/fW | −0.36 | −0.42 | −0.35 |
| (6) ΣL2F/ΣL2R | 1.24 | 0.82 | 0.41 |

| Conditional expression | Example 7 | Example 8 | Example 9 |
|---|---|---|---|
| (1) f2/fW | −1.59 | −1.99 | −1.78 |
| (2) f2F/f2 | 12.80 | 6.75 | 18.52 |
| (3) Σd2/D2 | 0.51 | 0.54 | 0.55 |
| (4) N2 | 2 | 2 | 1.88 |
| (5) P2/fW | −0.33 | −0.28 | −0.27 |
| (6) ΣL2F/ΣL2R | 0.81 | 0.43 | 0.42 |

| Conditional expression | Example 10 |
|---|---|
| (1) f2/fW | −1.68 |
| (2) f2F/f2 | — |
| (3) Σd2/D2 | 0.46 |
| (4) N2 | 1.86 |
| (5) P2/fW | −0.34 |
| (6) ΣL2F/ΣL2R | — |

The embodiment and various examples of the present invention are described above. However, the present invention is not restricted to these embodiment and examples, and embodiments formed by combining arrangement of these embodiment and examples without departing from the scope of the present invention are also included in the category of the present invention.

The endoscope objective optical system according to the present embodiment shows an effect of having a thin diameter and a favorable imaging performance, while enabling a magnified observation and a normal observation.

What is claimed is:

1. An endoscope objective optical system comprising, in order from an object side:
    a first lens group having a positive refractive power;
    a second lens group having a negative refractive power; and
    a third lens group having a positive refractive power, wherein:
    a lens surface positioned nearest to an image side in the second lens group is a concave surface which is directed toward the image side,
    the second lens group moves along an optical axis, and
    the following conditional expressions (1) and (3) are satisfied:

$$-2.1 < f2/fW < -1 \quad (1)$$

$$0.45 < \Sigma d2/D2 < 0.64 \quad (3)$$

where,
    f2 denotes a focal length of the second lens group,
    fW denotes a focal length of the overall endoscope objective optical system at a time of a normal observation,
    $\Sigma d2$ denotes a thickness of the second lens group, and
    D2 denotes a distance from a lens surface positioned nearest to the image side in the first lens group up to a lens surface positioned nearest to the object side in the third lens group.

2. The endoscope objective optical system according to claim 1, wherein the following conditional expression (5) is satisfied:

$$-0.55 < P2/fW < -0.22 \quad (5)$$

where,
    P2 denotes Petzval's sum for the second lens group, and
    fW denotes the focal length of the overall endoscope objective optical system at the time of normal observation.

3. The endoscope objective optical system according to claim 2, wherein the following conditional expression (6) is satisfied:

$$0.4 < \Sigma L2F/\Sigma L2R < 1.25 \quad (6)$$

where,
    $\Sigma L2F$ denotes a sum of an air-conversion length of lenses in the front group, and
    $\Sigma L2R$ denotes a sum of an air-conversion length of lenses in the rear group.

4. An endoscope objective optical system comprising, in order from an object side:
    a first lens group having a positive refractive power;
    a second lens group having a negative refractive power; and
    a third lens group having a positive refractive power, wherein:
    the second lens group comprises, in order from the object side, a front group, an aperture stop, and a rear group, and
    a lens surface positioned nearest to the object side in the second lens group is a concave surface which is directed toward the object side, and
    a lens surface positioned nearest to an image side in the second lens group is a concave surface which is directed toward the image side, and
    the second lens group moves along an optical axis.

5. The endoscope objective optical system according to claim 4, wherein the following conditional expressions (1), (2), and (3) are satisfied:

$$-2.1 < f2/fW < -1 \quad (1)$$

$$-37 < f2F/f2 < 19 \quad (2)$$

$$0.45 < \Sigma d2/D2 < 0.64 \quad (3)$$

where,
    f2 denotes a focal length of the second lens group,
    fW denotes a focal length of the overall endoscope objective optical system at the time of normal observation,
    f2F denotes a focal length of the front group,
    $\Sigma d2$ denotes a thickness of the second lens group, and
    D2 denotes a distance from a lens surface positioned nearest to an image side in the first lens group up to a lens surface positioned nearest to an object side in the third lens group.

6. The endoscope objective optical system according to claim 5, wherein:
    the second lens group includes at least one predetermined lens, and
    the predetermined lens is a planoconcave lens or a meniscus lens, and
    the following conditional expression (4) is satisfied:

$$1.85 < N2 \quad (4)$$

where,
    N2 denotes a refractive index for an e-line of the predetermined lens.

7. The endoscope objective optical system according to claim 6, wherein the following conditional expression (5) is satisfied:

$$-0.55 < P2/fW < -0.22 \quad (5)$$

where,
    P2 denotes Petzval's sum for the second lens group, and
    fW denotes the focal length of the overall endoscope objective optical system at the time of normal observation.

* * * * *